United States Patent [19]
Hutchinson

[11] Patent Number: 5,889,110
[45] Date of Patent: Mar. 30, 1999

[54] SALTS OF PEPTIDES WITH CARBOXY-TERMINATED POLYESTERS

[75] Inventor: Francis Gowland Hutchinson, Lymm, England

[73] Assignee: Zeneca Limited, London, United Kingdom

[21] Appl. No.: 473,303

[22] Filed: Jun. 7, 1995

Related U.S. Application Data

[62] Division of Ser. No. 65,771, May 24, 1993, abandoned.

[30] Foreign Application Priority Data

May 28, 1992 [GB] United Kingdom .................. 9211268

[51] Int. Cl.$^6$ .............................. A61K 9/16; A61K 9/52; A61K 37/02; B32B 5/16
[52] U.S. Cl. ..................... 525/54.1; 514/2; 514/772.3; 514/772.6; 514/800; 514/806; 514/807; 514/808; 514/809; 514/963; 424/489; 424/492; 424/499; 435/180; 435/181; 435/182; 428/402.24
[58] Field of Search ............................... 525/54.1; 514/2, 514/772.3, 772.6, 800, 806, 807, 808, 809, 963; 424/489, 497, 499; 435/180, 181, 182; 436/531, 532, 533, 534; 428/402.24

[56] References Cited

U.S. PATENT DOCUMENTS

| | | | |
|---|---|---|---|
| 4,675,189 | 6/1987 | Kent et al. | 424/78 |
| 4,767,628 | 8/1988 | Hutchinson | 424/78 |
| 4,938,763 | 7/1990 | Dunn et al. | 424/78 |
| 4,997,643 | 3/1991 | Partain, III et al. | 424/78 |
| 5,005,602 | 4/1991 | Hutchinson | 424/78 |
| 5,672,659 | 9/1997 | Shalaby et al. | 525/54.1 |

FOREIGN PATENT DOCUMENTS

| | | |
|---|---|---|
| 0 052510 | 5/1982 | European Pat. Off. . |
| 0 058481 | 8/1982 | European Pat. Off. . |
| 0 350246 | 1/1990 | European Pat. Off. . |
| 0 467389 | 1/1992 | European Pat. Off. . |
| 2234169 | 1/1991 | United Kingdom . |
| 9101126 | 2/1991 | WIPO . |
| 9200718 | 1/1992 | WIPO . |

OTHER PUBLICATIONS

F. G. Hutchinson et al., "Biodegradable Polymers for the Delivery of Polypeptides and Proteins"; Ziekenhuisfarmacie; vol. 4, No. 2, 1988, pp. 54–56.

Lawter et al., Proc. Int. Symp. Control. Rel. Bioact. Mater., 14 (1987), pp. 99–100.

Okada et al., Pharmaceutical Research, 8 (5), 1991, pp. 587–587.

*Primary Examiner*—Nathan M. Nutter
*Attorney, Agent, or Firm*—Cushman Darby & Cushman, Intellectual Property Group of Pillsbury Madison & Sutro, LLP

[57] ABSTRACT

This invention relates to novel salts composed of a cation derived from a peptide containing at least one basic group and an anion derived from a carboxy-terminated polyester, processes for the manufacture of such salts, and the use of such salts in the manufacture of extended release pharmaceutical compositions. The salts of the invention possess a variety of properties which are useful in the formulation of extended release pharmaceutical compositions, whether the salts are in pure form or are in admixture with either an excess of the peptide in its free, unbound form or an excess of the free polyester.

47 Claims, No Drawings

SALTS OF PEPTIDES WITH CARBOXY-TERMINATED POLYESTERS

This is a division of application Ser. No. 08/065,771, filed May 24, 1993 abandoned.

This invention relates to novel salts composed of a cation derived from a peptide containing at least one basic group and an anion derived from a carboxy-terminated polyester, processes for the manufacture of such salts, and the use of such salts in the manufacture of extended release pharmaceutical compositions. The salts of the invention possess a variety of properties which are useful in the formulation of extended release pharmaceutical compositions, whether the salts are in pure form or are in admixture with either an excess of the peptide in its free, unbound form or an excess of the free polyester. Such salts are amphipathic, being comprised in part of a peptide, which is hydrophilic and lipophobic, and in part a polyester, which is hydrophobic and lipophilic.

The word "peptide" is used herein in a generic sense to include poly(amino acids) which are normally generally referred to as "peptides", "polypeptides" or "proteins"; and a "basic peptide" is a peptide which is basic in nature, arising from the presence of an excess of basic amino acids, for example arginine or lysine, or arising from the N-terminus of the peptide, or simply a peptide which contains at least one basic group, optionally in the presence of one or more acidic amino acid groups. The term also includes synthetic analogues of peptides, unnatural amino acids having basic functionality, or any other form of introduced basicity. The word "polyester" is used hereinafter to mean a carboxy-terminated polyester.

European Patent No. 58,481 alludes to the possibility of specific chemical interactions between the terminal carboxylic acid group of a polyester and a basic group or groups within a peptide. Lawter et al., Proc. Int. Symp. Control Rel. Bioact. Mater., 14, 19, (1987) and Okada et al., Pharmaceutical Research, 8, 584–587 (1991), also refer to this possibility, but these publications are speculative in this regard, in that they do not particularly describe any such specific peptide-polyester salt, do not give any indication of how such salts can be prepared, and are silent with regard to any beneficial effects which could arise from the use of such salts in the manufacture of pharmaceutical compositions.

According to the present invention, however, there is provided a composition containing or comprising, as initially made, a salt formed from a cation derived from a peptide containing at least one basic group and an anion derived from a carboxy-terminated polyester; the composition being in the form of a solution or dispersion of the salt in a solvent which is a solvent for the free polyester but not a solvent for the free peptide, the particle size of the salt in said dispersion being less than 5 μm and preferably less than 0.2 μm; or in the form of microparticles or an implant for injection or sub-dermal implantation.

The cation component of the salt may be derived from a basic peptide which is pharmacologically active, or from a basic peptide which is pharmacologically inactive. When the basic peptide is pharmacologically active, the salt of the invention itself may be formulated into an extended release pharmaceutical formulation. When the basic peptide is pharmacologically inactive, the salt of the invention may be used as an excipient in the formulation of extended release compositions of other, pharmacologically active, peptides which either are acidic in nature, (comprising an excess of acidic amino acids such as aspartic acid and glutamic acid), or are neutral in nature.

In extended release formulations of peptides, a further requirement, of course, is that the peptide should be substantially stable in the formulation over the period of release envisaged. By "substantially stable" it is meant that the drug is not rendered totally insoluble or denatured, with total loss of pharmacological activity, during the period of use envisaged for the formulation.

Suitable pharmacologically active peptides have a molecular weight of at least 300 Da, and preferably at least 800 Da. Examples of such peptides which may be substantially stable in the extended release formulations over the intended period of release, and which may therefore be used in the compositions of this invention, are oxytocin, vasopressin, adrenocorticotrophic hormone (ACTH), epidermal growth factor (EGF), prolactin, luteinising hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumour necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factor VII and IX, lysozyme chloride, renin, bradykinin, tyrocidin, gramicidines, growth hormones, melanocyte stimulating hormone, thyroid hormone releasing hormone, thyroid stimulating hormone, parathyroid hormone, pancreozymin, cholecystokinin, human placental lactogen, human chorionic gonadotrophin, protein synthesis stimulating peptide, gastric inhibitory peptide, vasoactive intestinal peptide, platelet derived growth factor, growth hormone releasing factor, bone morphogenic protein, and synthetic analogues and modifications and pharmacologically-active fragments thereof.

Preferred peptide components of the compositions of the invention are synthetic analogues of LHRH, and particular such analogues include, but are not limited to, buserelin ([D-Ser(Bu$^t$)$^6$, des-Gly-NH$_2$$^{10}$]-LHRH(1–9)NHEt), deslorelin ([D-Trp$^6$, des-Gly-NH$_2$$^{10}$]-LHRH(1–9)NHEt), fertirelin ([des-Gly-NH$_2$$^{10}$]-LHRH(1–9)NHEt), goserelin ([D-Ser(Bu$^t$)$^6$, Azgly$^{10}$]-LHRH), histrelin ([D-His(Bzl)$^6$, des-Gly-NH$_2$$^{10}$]-LHRH(1–9)NHEt), leuprorelin ([D-Leu$^6$, des-Gly-NH$_2$$^{10}$]-LHRH(1–9)NHEt), lutrelin ([D-Trp$^6$, MeLeu$^7$, des-Gly-NH$_2$$^{10}$]-LHRH(1–9)NHEt), nafarelin ([D-Nal$^6$]-LHRH), tryptorelin ([D-Trp$^6$]-LHRH), and pharmacologically active salts thereof.

Suitable pharmacologically inactive basic peptides, which may be used in the salts of the invention, are polyarginine, polylysine and poly(arginine-co-lysine), (co-) polymers of neutral amino acids, in D-, L- or DL-form, with arginine and/or lysine in D-, L- or racemic form, or peptides or (co-)polypeptides in which the peptide chains are terminated in whole or in part by a basic group at the N-terminus and the backbone is comprised of neutral amino acid residues.

The carboxy-terminated polyester used as the source of the anion in the salt of the invention may be a homo-polyester or a co-polyester. Preferred such polyesters are those which degrade or erode in an aqueous physiological environment, such as that found in intramuscular or subcutaneous tissue, to low molecular weight water-soluble fragments. In this environment, the dominant process of degradation is simple bulk hydrolysis, involving hydrolytic scission of ester groups, which leads to lower molecular weight homo- or co-polyester fragments, and ultimately to the disappearance of the formulation from the site of administration. However, it is recognised that at these injection or implantation sites, as well as at other sites in living tissue, other degradation mechanisms may be involved such as those mediated by enzymes.

Suitable homo- and co-polyesters are those derived from hydroxy-acids or from the polycondensation of diols and/or polyols, for example (but not limited to) polyethylene glycols, polypropylene glycols, 2–10C alkylene glycols, glycerol, trimethylolpropane, and polyoxyethylated forms of polyfunctional alcohols such as glycerol, trimethylolpropane and sugars, with dicarboxylic acids and/or polycarboxylic acids, for example (but not limited to) (1–10C alkane)dicarboxylic acids, particularly malonic, succinic and glutaric acids, phthalic acids, mellitic and pyromellitic acids, optionally in the presence of hydroxy acid(s) and/or mono-ols.

The preferred methods of preparing homo- and co-polyesters based upon hydroxy acids are by ring opening polymerisation of the cyclic acid dimers or by direct polycondensation or co-polycondensation of the hydroxy acids or mixtures of the hydroxy acids, or lactones derived from such hydroxy acids. These polymerisations, both of the ring opening type or the polycondensation type, are preferably carried out so that the resulting homo- or co-polyesters contain, in whole or in part, polymer chains having carboxylic acid functionality. Thus the ring opening polycondensation of the acid dimers is carried out in the presence of an appropriate polymer chain transfer agent or co-initiator which controls both the molecular weight and the structure of the resulting homo- or co-polyester. Suitable such transfer agents are water, hydroxycarboxylic acids, monocarboxylic acids, dicarboxylic acids and polycarboxylic acids.

For polyesters prepared by polycondensation or co-polycondensation, the polymerisation is carried out under conditions such that an excess of carboxylic acid functionality is used, that is, the ratio of [—COOH] to [—OH] is equal to or greater than 1. The structure and molecular weight of the polycondensate are determined by the nature of the alcohols used (whether mono-ols, diols or polyols, or a mixture), tne nature of the acids used (whether mono-, di- or polycarboxylic acids, or a mixture), and the amount of the excess of carboxylic acid used. Acids involved in the Krebs cycle are particularly useful.

Examples of suitable hydroxy acids or lactones, which may be used to manufacture homo- or co-polyesters useful in this invention, include β-propionolactone, β-butyrolactone, γ-butyrolactone and pivalolactone, and α-hydroxybutyric acid, α-hydroxyisobutyric acid, α-hydroxyvaleric acid, α-hydroxyisovaleric acid, α-hydroxycaproic acid, α-hydroxyisocaproic acid, α-hydroxy-β-methylvaleric acid, α-hydroxyheptanoic acid, α-hydroxydecanoic acid, α-hydroxymyristic acid and α-hydroxystearic acid. Preferred such homo- and co-polyesters are those derived from lactic acid in its D-, L- or DL- form, and glycolic acid, or the corresponding dimers lactide and glycolide, and a preferred optional chain stopper is lactic acid.

Although a macromolecular, basic peptide drug can exist wholly or in part as a polymer-cation, and a polyester can exist wholly or in part as a polymer-anion, salt formation arising from acid-base interaction between such polymeric species, using conventional processes of mixing, or using organic solvents, is extremely difficult or even impossible. For example, melt mixing the two components is unsuitable, since it is well known that peptides do not normally melt, but rather decompose at the elevated temperatures commonly used to melt polymers. However, even if the peptide were to melt (which it does not), it would be incompatible with, or insoluble in, a homo- or co-polyester for thermodynamic reasons, as follows.

Peptides are macromolecules, and so possess many of the typical properties of conventional polymers. They are therefore (in the absence of specific chemical or physical interactions) totally incompatible with, or insoluble in, other macromolecules which have different chemical and polymer backbone structure, as the free energy of mixing of the two dissimilar polymer types is highly positive and so is not thermo-dynamically favoured. In the bulk state, peptides are highly polar and strongly hydrogen bonded molecules, with the result that the enthalpy of mixing of peptides with homo- or co-polyesters (which are relatively non-polar, and in which hydrogen bonding is either absent or weak) is highly positive; that is, endothermic and thermodynamically not favoured. Further, macromolecules are by definition large, and so have a low intrinsic entropy, resulting in the entropy of mixing of two different macromolecular species being very low or even negative. (See, for example, P J Florey, "Principles of Polymer Chemistry", Cornell University, 1953 at 555; L Bohn, "Polymer Handbook", 2nd Edition, J Wiley 1975, III-211; and L Bohn, Rubber Chemistry and Technology, 1966, 493). Consequently, the mixing of a peptide with a polyester at elevated temperature in the molten state will not give rise to the mixing on the molecular scale necessary for salt formation to occur. Simple admixture of a peptide and a polyester, therefore, does not give rise to salt formation.

Similar difficulties exist with attempts to form salts of peptides and polyesters using organic solvents, unless the peptide has some solubility or swellability in the solvent. The solubility properties of polyesters and peptides are totally different. Solvents which dissolve the peptide, such as water, are complete non-solvents for the polyester; and, in general, good solvents for the polyester, such as dichloromethane, are complete non-solvents for the peptide. Those solvents which can dissolve both the peptide and the polyester, such as dimethylsulfoxide, dimethylformamide, dimethylacetamide and N-methylpyrrolidone, have different problems because they are relatively non-volatile, have high boiling points, and so are extremely difficult to remove, and also because of the unacceptable toxicity of some of these solvents. It has been possible to identify certain solvents for both components which are more volatile and which are toxicologically acceptable, but such solvents present other difficulties. For example, acetic acid is a solvent for both peptides and polyesters, but the use of a large amount of acid solvent predisposes the peptide to exist as the acetate salt (because of mass action effects), so that the removal of the acetic acid at room temperature (say 20°–25° C.), or by freeze drying, results in phase separation of the peptide and the polyester, so that the desired salt formation tends not to occur.

It is an object of the present invention, therefore, to provide a process for the manufacture of a salt, comprising a cation of a basic peptide and an anion of a carboxy-terminated polyester.

The preparation of the peptide-polyester salts of this invention can be carried out using homo- or co-polyesters containing carboxylic acid groups, and peptides wherein the basic residues occur as the free base or as salts of a weak acid, preferably a volatile acid, having an acid dissociation constant of less than $10^{-3}$ or a $pK_a$ ($pK_a = -\log_{10} K_a$, where $K_a$ is the acid dissociation constant) of greater than 3. A particularly preferred such basic peptide salt is a salt with acetic acid. However, because of the inherent incompatibility of the two macromolecular species, particular conditions have to be used in which these peptide-polyester salts can be generated.

One means of achieving this is to use a solvent which dissolves both the peptide and the polyester, to form a solution, from which the solvent can be removed directly, leaving either firstly the amphipathic salt, or secondly a mixture of polyester and peptide in a physical state which is predisposed to form the amphipathic salt when processed further.

An example of the first approach is to use solvents such as, but not limited to, dimethylsulfoxide, dimethylformamide, dimethylacetamide and N-methylpyrrolidone, which are essentially neutral and which can be solvents for both the peptide and the polyester. Under normal circumstances, as indicated above, these solvents are extremely difficult to remove, due to their high boiling points and relative non-volatility. When a peptide (for example as an acetate salt) and a polyester are dissolved in one of these solvents, the peptide tends to exist as the salt with the polyester, as the more strongly acidic lactic or glycolic acid group in the polyester displaces the weaker carboxylic acid. The bulk of the solvent and liberated acetic acid (or other weak but volatile carboxylic acid) may be removed in vacuo, and the residual solution containing peptide-polyester salt is added to distilled water, to precipitate the insoluble polymeric salt.

The distilled water is preferably carbon dioxide-free, to avoid the formation of carbonate salts by displacement of the polyester anion. Residual solvent in the peptide-polyester salt may then be removed by further washing with water, also preferably carbon dioxide-free. In some circumstances, the polymeric salt may be isolated by direct precipitation into water, without any need to remove any solvent, and this approach is particularly useful when the peptide is used as the base.

Thus, according to a further feature of this invention, there is provided a process for the manufacture of a salt comprising a basic peptide and a carboxy-terminated polyester, which comprises dissolving the basic peptide, in free base form or in the form of a salt with a weak acid, for example acetic acid, and the carboxy-terminated polyester in a neutral, polar solvent in which both are soluble, removing the solvent or most of the solvent, and adding the remaining concentrated solution to an excess of a non-solvent for the peptide-polyester salt.

The second approach, also based on using a solvent which dissolves both the peptide and the polyester, relies on said solvent being capable of removal by freezing and conventional freeze drying, or by spray drying. An essential part of this process is the removal of the solvent from the peptide-polyester mixture at an extremely rapid, almost instantaneous, rate, and preferably at a temperature which is below the glass transition temperature of the polyester and the peptide. In this case, the solvent may be neutral or acidic, and a preferred solvent is acetic acid.

Such extremely rapid removal of solvent from a solution which exhibits some degree of viscous flow or visco-elastic behaviour results in phase separation of the two incompatible macromolecular types occurring on an extremely small colloidal scale. That is, the resulting peptide-polyester mixture has an extremely high surface area and surface energy. As a consequence, when another different solvent for the polyester, which is normally a non-solvent for the peptide, is added to essentially solvent-free peptide-polyester mixtures of this type, the high surface energy is dissipated by salt formation, and the disappearance of the colloidal nature of the peptide in the polyester. Suitable solvents for this second approach have to be freeze dryable and include, but are not limited to, acetic acid, dioxan/water mixtures and tert-butanol/water mixtures, or have to be spray dryable.

Thus, according to a further feature of this invention, there is provided a process for the manufacture of a salt comprising a basic peptide and a carboxy-terminated polyester, which comprises dissolving the basic peptide, in free base form or in the form of a salt with a weak acid, for example acetic acid, and the carboxy-terminated polyester in a solvent in which both are soluble, and which is capable of being removed by freeze-drying, freezing the resulting solution at high speed, freeze-drying the resulting frozen mixture, dispersing the resulting mixture in a solvent for the polyester component, and allowing the mixture to dissolve as the peptide-polyester salt is formed.

More particularly, in this process the solution of the peptide and the polylactic acid, or a co-polymer of lactic and glycolic acids, in acetic acid is added to liquid nitrogen in a dropwise fashion. This results in a more or less instantaneous freezing of the acetic acid solution, and a more or less instantaneous generation of an essentially solvent-free peptide-polyester mixture. Freeze-drying to remove the acetic acid solvent gives a peptide-polyester product mixed on an extremely fine colloidal scale. For many peptides, the colloidal nature of such a material is demonstrated when a solvent for the polyester is added, for example dichloromethane, when an extremely fine colloidal suspension is generated, and providing there is an excess of carboxylic acid functionality in the mixture, a clear solution can be obtained eventually on standing, the excess surface energy being lost as peptide-polyester salt is formed. Other procedures to more or less instantly freeze the peptide/polyester/acetic acid mixture may be used in place of dropwise addition to liquid nitrogen, for example dropping the mixture into a mixture of solid carbon dioxide and hexane.

Hypothetically, of course, a totally insoluble compound can be made to be soluble if it can be reduced to a sufficiently small average particle size. If it is assumed that the particle is a sphere of radius r, having density $\sigma$, and that it has a surface energy $\gamma$, such a particle will have a surface energy $4\pi r^2 \gamma$ associated with it. It will also have a mass of $^4/_3 .\pi r^3 \sigma$ and so the surface energy per unit mass is $^{3\pi\gamma}/_{\sigma r}$. Consider now two cases of saturated solutions:

(i) when excess solid is extremely coarse and therefore has very little surface energy and the saturated solution has a concentration $C_s$. Then the Gibbs free energy is:

$$G^1_{solution} = G_0 + RT\ln C_s = G^1_{solid};$$

(ii) when the excess solid is extremely small particles of radius r, the Gibbs free energy of the solution which is in equilibrium with extremely small particles is:

$$G^2_{solution} = G_0 + RT\ln C$$

but in this case the solid has a Gibbs free energy of $$G^1_{solid} + {}^{3\pi\gamma}/_{\sigma r},$$

and $$G^2_{solution} = G_0 + RT\ln C = G^1_{solid} + {}^{3\pi\gamma}/_{\sigma r},$$

or $$G^1_{solid} = G_0 + RT\ln C - {}^{3\pi\gamma}/_{\sigma r}.$$

But from (i) above, $$G^1_{solid} = G_0 + RT \ln C_s,$$

and therefore $$G_0 + RT \ln C^{-3\pi\gamma/\sigma r} = G_0 + RT \ln C_s,$$

or $$C = C_s \cdot e^{3\pi\gamma/\sigma r}$$

so that, as r decreases, C (hypothetically) increases.

In the usual case, higher than normal solubility due to small particle size is metastable, and the particles grow in size, for example by dissolution and recrystallisation, so that the effect of high surface energy is negated. However, with small particle size peptide-polyester mixtures, salt formation can occur, and this offers an alternative means of reducing the surface energy of the colloidal particles by allowing the formation of a soluble amphipathic salt, which as a solution offers the lowest free energy condition.

According to a further feature of the invention, there is provided a process for the manufacture of a salt comprising a basic peptide and a carboxy-terminated polyester, which comprises reacting a basic peptide in the form of a salt with a strong acid, such as a chloride or sulfate, with a polyester wherein some or all of the polyester is in the form of a carboxylic acid salt with a suitable alkali metal or alkaline earth metal, for example a sodium, potassium, calcium or magnesium carboxylate salt. For low molecular weight polyesters, (having a weight average molecular weight of less than about 10,000), the salts with alkalis can be dissolved, or very finely dispersed, in water. Addition of such a solution or dispersion to an aqueous solution (preferably free of carbon dioxide) of the peptide, results in precipitation of the water-insoluble amphipathic peptide-polyester salt.

In a similar way, the chloride or sulfate salts of 'pegylated' basic peptides (polyoxyethylene conjugates of peptides) are, or can be, partially compatible with, or soluble in, solvents such as dichloromethane, and the sodium or potassium salts of carboxy-terminated polyesters can also be soluble in dichloromethane. Thus, when two such salts are mixed in the appropriate proportions, the soluble peptide-polyester salt is generated by double decomposition, with precipitation of the alkali metal chloride or sulfate.

The thermodynamic incompatibility of different macromolecules, referred to above, has been known for many years, but it has rarely entered into any consideration in the prior art of the extended release of peptide drugs from polyester matrixes. A necessary consequence of this thermodynamic incompatibility, or insolubility, is that in normal circumstances polyesters are totally impermeable to peptide drugs. For partition-dependent Fickian diffusion of a peptide drug through a polyester to occur, the peptide must have some solubility in the polyester. However, for the reasons discussed above, this is not the case, and so transport of the peptide through the polyester by partition-dependent Fickian diffusion is impossible.

Furthermore, even if, for the sake of argument, the peptide drug, or one of its synthetic analogues, had some solubility in or compatibility with the polyester, transport by diffusion through the polyester phase would still be impossible. It has long been recognised that the free volume in the polyester, which arises from rotational and translational polyester segment mobility, and which should allow the passage of diffusing molecules, is insufficiently large to accommodate the diffusion of macromolecules having molecular weights greater than about 500 Da or so. (See, for example, R W Baker and H K Lonsdale, "Controlled Release: Mechanisms and Rates" in "Controlled Release of Biologically Active Agents, ed. A C Tanquary and R E Lacey, Plenum Press, 1974, 15 et seq.)

However, even though transport of a peptide drug through a polyester by Fickian diffusion is essentially impossible for peptides of more than about 500 Da or so, continuous release of polypeptides has nevertheless been achieved. European Patent No. 58,481 discloses how continuous release of a peptide drug from a polyester was obtained by using the very different properties of the two macromolecules, peptides being hydrophilic and water-soluble, and polyesters being hydrophobic and water-insoluble. In the formulations described in that patent, peptide drug release was achieved primarily through aqueous pores, which are generated initially by simple leaching of peptide from domains at the surface of the formulation, or from domains of peptide drug which are continuous or contiguous with the surface of the formulation. This leaching provides for an initial phase of release, and subsequent bulk hydrolytic degradation of the polyester results in the generation of further porosity within the polyester, and so further peptide release, governed by degradation and erosion, can occur. If the porosity arising from hydrolytic polyester degradation does not occur quickly enough, the initial release from the leaching phase is complete before sufficient degradation-induced porosity is generated in the delivery system, and discontinuous release of the peptide is obtained. The parameters of the formulations disclosed in EP 58,481 were therefore chosen so that hydrolytic degradation of the polyester occurred at the right time in relation to the initial leaching release phase, so as to ensure that the two phases of release overlapped, resulting in continuous release of the peptide drug.

However, whereas Fickian diffusional transport of a peptide through the polyester phase is impossible in the case of those simple peptide-polyester mixtures, a totally different situation arises in the case of formulations of the peptide-polyester salts of the present invention, optionally in the presence of free polymer. In formulations containing these materials, there is no separate phase consisting of polyester alone; rather, the continuous phase which controls release of the peptide is wholly or in part the peptide-polyester salt. Free peptide has some solubility in this phase of peptide-polyester salt, and so in formulations using such materials, true Fickian, partition-dependent diffusion of a peptide is possible, if the other requirements, such as effective free volume, are present.

Because the peptide-polyester salt contains a highly hydrophilic segment, the peptide-polyester salt formulation has a much higher water uptake than the polyester alone. Furthermore, in these formulations the water uptake is enhanced even more, due to the ionic nature of the peptide-polyester interaction, and the solvation of ions or ion pairs in the macromolecular salt by water. This implies an essentially hydrogel nature for the peptide-polyester salt, and provides an increase in the degrees of mobility of macromolecular segments in the polycation-polyanion complex. That is, the effective free volume of the matrix material is increased, and so can accommodate a macromolecular peptide.

The net effect of these properties of the peptide-polyester salt, (optionally in the presence of free polymer), is to allow Fickian diffusional transport of a macromolecular peptide through the matrix of peptide-polyester salt or the mixed salt and free polymer phase. This is a totally different situation from that which occurs with polyester alone, or with simple admixtures of peptides and polyesters, and so extended release matrixes or membranes based on the increased permeability arising from the use of the peptide-polyester salt are central to the formulations for the controlled release of peptides described hereafter in this application.

The peptide-polyester salts of the present invention thus provide new and unexpected advantages in the design of parenteral drug delivery systems, based on solutions or dispersions using various mixtures of free peptide drugs, free polyester and peptide-polyester salt, in both aqueous and non-aqueous pharmaceutically acceptable injection vehicles, and based on sub-dermal implants which can be injected, intramuscularly or sub-cutaneously, or implanted, by virtue of the novel and unexpected solubility of these peptide-containing moieties in lipophilic solvents. Furthermore, formulations based on these peptide-polyester salts, in particular those using highly lipophilic polyesters, can also be administered by other routes. Of particular importance is the oral route, in which the various combinations of peptide-polyester salt and/or free peptide drug and/or free polyester can be used to good effect. In many instances, for oral administration it is preferred to use a pharmaceutically acceptable carrier such as a vegetable oil or a variant thereof, and including mono-, di- and tri-glycerides either alone or in admixture with other oils. Of less importance are the topical, rectal and intranasal routes of administration.

Other than European Patent No. 58,481 (1982), referred to above, Lawter et al. (loc. cit.) and Okada et al. (loc. cit.) are the only state of the art known to the applicants herein which refers to the possibility of obtaining peptide-polyester salts, but both these publications are speculative, in that they do not disclose how this putative interaction can be realised or utilized. It is a further object of the present invention to provide extended release pharmaceutical formulations, comprising various combinations of peptide-polyester salt and/or free peptide drug and/or free polyester in various proportions to give at least three different profiles of controlled drug release.

Thus, according to a further feature of the invention there is provided an extended release pharmaceutical composition comprising a peptide-polyester salt, as defined above, and/or free peptide drug and/or free polyester, and optionally other pharmaceutical excipient or excipients.

The design of the pharmaceutical compositions of this invention is based upon the following considerations. Whereas a simple peptide drug is normally soluble in water, both its salt with a polyester, and the free polyester itself, are normally totally water-insoluble, (although it is recognised that, for very low oligomeric forms of polyesters and co-polyesters, whilst they may themselves be water-insoluble, they may be water-soluble when in the form of a peptide-polyester salt). However, incubation of a mixture of a peptide drug and a polyester, wherein all or part of the peptide is present as the peptide-polyester salt, in aqueous physiological fluids, results in some degradation of the polyester. If these degraded products are water-insoluble, then the degrading peptide-polyester salt will continue to be insoluble. On the other hand, if the polyester is of sufficiently low molecular weight initially, or contains a polymeric component of equally or similarly low molecular weight, such that water-soluble polyester-derived acidic fragments are produced, then these fragments (as anions) are co-transportable with the polypeptide cation. It has been shown for the new peptide-polyester salt compositions of this invention that immediacy of release is strongly dependent on the molecular weight and molecular weight distribution of the polyester component.

Molecular weight distribution is defined as $M_w/M_n$ where $$M_w \text{ (weight average molecular weight)} = \frac{\Sigma w_i \cdot M_i}{\Sigma w_i} = \frac{\Sigma n_i \cdot M_i^2}{\Sigma n_i \cdot M_i}$$

and $$M_n \text{ (number average molecular weight)} = \frac{\Sigma n_i \cdot M_i}{\Sigma n_i}$$

and where $w_i$ is the weight fraction of polymer molecules having a molecular weight $M_i$, and $n_i$ is the number of polymer molecules having molecular weight $M_i$.

Molecular weight distribution is often referred to as poly-dispersity, and the various values for narrow, normal or most probable, and wide distribution are well known (see, for example, "Polymer Handbook", 2nd Edition, J Wiley 1975, IV-3.) It is generally accepted that a polydispersity of less than 1.8 is a narrow distribution or low polydispersity, approximately 1.8 to 2.2 is a normal or most probable distribution or normal polydispersity, and more than approximately 2.2 is a wide or broad distribution or high polydispersity.

For the administration of peptide drugs by the parenteral route, such as intramuscular or sub-cutaneous injection or sub-dermal implantation of a depot or delivery system, polyesters having a number average molecular weight of more than 2000 Da, or an inherent viscosity at 1% w/v at 25° C. in chloroform of more than or equal to 0.08 dl/g, and up to and including 4.0 dl/g, are preferred. For administration by other routes, such as orally, the preferred range of number average molecular weight is 500 to 500 Da.

It is obvious from the above considerations, which have largely been ignored in the state of the art, that the degradation of the polyesters, particularly in the presence of basic peptide, to give even a small fraction of water-soluble derived fragments, and the time interval for this to occur, will be controlled by molecular weight and molecular weight distribution. Essentially immediate degradation to water-soluble fragments occurs using both narrow and normal distribution polyesters, having weight average molecular weights of less than about 10,000 Da and less than about 15,000 Da respectively (depending on the type of molecular weight distribution), but in general the lower the polydispersity of the polyester the lower the weight average molecular weight required for immediate degradation to water-soluble fragments. For polyesters of weight average molecular weight of greater than 15,000 Da, normal or wide distributions are required. Again this depends in part on the nature and type of the molecular weight distribution, but in general the higher the weight average molecular weight, the higher the polydispersity needed in order to achieve early degradation to water-soluble fragments.

For polyester or co-polyester and peptide compositions where some or all the peptide is in the form of a peptide-polyester salt, optionally containing free polyester, three different release profiles can be obtained. The first of these is when degradation of the polyester occurs to give essentially immediate generation of acidic water-soluble or hydrophilic fragments, which results in immediate release of peptide according to the following mechanism:

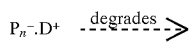

polymer/drug salt which is totally insol-
uble in water

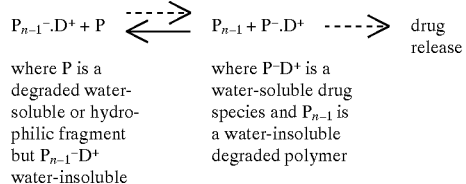

where P is a degraded water-soluble or hydrophilic fragment but $P_{n-1}^{-}D^{+}$ water-insoluble where $P^{-}D^{+}$ is a water-soluble drug species and $P_{n-1}$ is a water-insoluble degraded polymer (P = a water-soluble degraded polyester fragment, or a hydriphilic water-insoluble degraded polyester fragment which is made water soluble when present in the form of a salt with the basic peptide.
D = basic peptide.)

In this first case, the composition either may contain all the drug as peptide-polyester salt, or it may contain some free, unbound drug in addition to some peptide-polyester salt, in both cases also optionally in the presence of free polymer. However, the polymer degrades to water-soluble fragments, in the presence of peptide, almost immediately, with the consequence that almost immediate sustained continuous release of the peptide commences. It is to be noted that the diffusion of the free water-soluble peptide through the degrading composition is facilitated by the increased permeability of the matrix due to the presence of the peptide-polyester salt in the continuous phase that modulates release.

The second of these cases is when all the peptide drug is present as the peptide-polyester salt (optionally in the presence of free polyester), but the polyester does not degrade immediately to water-soluble fragments. This results in an initial interval in which there is no release of peptide drug. Even though the peptide-polyester salt confers on the matrix increased permeability to free diffusing peptide, there is no free peptide drug available to diffuse. All the peptide is in the form of a water-insoluble peptide-polyester salt, and it is only after some considerable time that the polyester degrades to water-soluble fragments and gives rise to free and transportable drug. This results in an extended induction period, during which there is initially no peptide release, following which induction period, release commences. This second case is ideal for timed and pulsed release of soluble vaccines and peptides.

The third case is when a formulation, based on a peptide-polyester drug system which contains a peptide drug both in its free form and in the form of a polymer-drug salt, optionally also in the presence of free polyester, and in which the polyester has a weight average molecular weight of greater than about 15,000 Da, (and preferably greater than about 30,000 Da), and having a narrow, or most probable, molecular weight distribution, is placed in a physiological environment, such as is found at intramuscular and subcutaneous injection sites, discontinuous release can result. A first phase of release arises because of the presence of free peptide drug, and its ability to be transported through the more permeable peptide-polyester salt system. If this first phase of release of free peptide-drug is complete before degradation of the polyester in the peptide-polyester salt occurs to give further free peptide drug, then discontinuous peptide drug release will ensue.

Obviously, if there is no interval in which free peptide drug is absent from the composition, during its degradation, then continuous release will be obtained. This release profile is similar to that disclosed in European Patent No. 58,481, but the mechanism of release in European Patent No. 58,481 and the materials used (no peptide-polyester salt) are quite different from the mechanisms and materials defined in this application. Depending on release profile these mixtures are ideal for continuous release of peptides, proteins and soluble vaccines.

As stated above, these peptide-polyester drug salt systems, their physicochemical characteristics and the mechanisms by which release of the peptide occurs, are quite different from those disclosed in European Patents Nos. 58,481 and 52,510, and all other publications relating to peptide release from homo- and co-polymers of lactic and glycolic acids, which are known to the inventor hereof. Of these only European Patent No. 58,481, Lawter et al (loc. cit.) and Okada et al (loc. cit.) make any reference to salt formation arising from the ionic interaction of polyester carboxylic acids groups and basic amino acids in peptides, but the composition made as described therein contain no peptide drug/polyester salt. These prior disclosures, however, are speculative in this regard, and do not establish conclusively that such interactions do indeed occur, nor do they demonstrate how such peptide-polyester salts can be prepared and isolated, and then used to effect the release of peptides, with a variety of different profiles of release, by virtue of their unexpected solubility in lipophilic organic solvents.

Amongst the properties of peptide-polyester mixtures that will determine release, and which have not been mentioned hitherto, are the number of basic functional groups in the peptide and the number of carboxylic acid groups in the polyester. The above-mentioned publications are also silent with regard to the remarkable and unexpected effects arising from the use of the peptide-polyester salts, and the surprisingly high permeability of systems containing, in whole or in part, the peptide-polyester salt, compared with the permeability of the polyester alone, or mixtures in which the two components are simply mixed, and which therefore contain no peptide-polyester salt.

This difference in permeability can be demonstrated in simple diffusion cell experiments, wherein a continuous and fault-free polyester membrane, separating two aqueous compartments, one containing an aqueous peptide solution and the other containing the aqueous phase alone, will not allow peptide transport across it, prior to significant degradation of the membrane polyester. In contrast, membranes containing, wholly or in part, the peptide-polyester salt allows drug transport across the salt-containing membrane by partition dependent diffusion, even if the peptide has a molecular weight of greater than 500 Da.

The peptide-polyester salts of the invention have many other surprising and useful advantageous properties, unknown in any similar prior art materials, which are particularly useful in the design and manufacture of pharmaceutical delivery systems. One of the most useful of these properties is the good solubility of the peptide, when in the form of a polyester salt, in organic solvents in which peptides are normally totally insoluble. This offers a great many advantages in pharmaceutical manufacture, in that it allows new processes and procedures to be used for the manufacture of drug delivery systems, and particularly facilitates aseptic manufacture. These processes and procedures, and the materials used, are totally different from the procedures and materials disclosed in the prior art.

Thus, solutions of a peptide-polyester salt, optionally containing free polymer, and/or free peptide in a solubilised or dispersed form, can be sterile-filtered, thus easing the problems normally associated with the sterile manufacture of solid or suspension peptide formulations. A sterile-filtered solution of a peptide-polyester salt can therefore be subjected to a variety of pharmaceutical drying procedures in an aseptic environment. Spray-drying, spray-congealing and other drying procedures which generate solid particles are preferred processes which readily lend themselves to aseptic operation.

Particularly useful is the generation of microparticles having particle sizes in the range from 0.2 $\mu$m to 500 $\mu$m, which can be suspended in a pharmaceutically acceptable injection vehicle. Such microparticles can be suspended in an aqueous injection vehicle prior to use, or alternatively in an organic injection vehicle which is a non-solvent for the materials used. For delivery systems based on homo- and co-polymers of lactic and glycolic acids, suitable such organic vehicles are highly lipophilic oils, such as (but not limited to) ethyl oleate, isopropyl myristate, vegetable oils and various fatty glycerides. In certain circumstances, it is preferred to use mixtures of such lipophilic vehicles.

Although such lipophilic vehicles are non-solvents for delivery forms based on lactic and glycolic acids, they are unsuitable for use with highly lipophilic polyesters such as those based on long chain hydroxy acids, for example hydroxystearic acids. For such highly lipophilic polyesters or co-polyesters, hydrophilic organic injection vehicles are preferred, such as (but not limited to) propylene glycol and low molecular weight polyethylene glycol. Obviously, aqueous injection vehicles are also suitable for delivery systems based on the more lipophilic polymers.

An alternative means of making microparticles utilises another unexpected and advantageous property of the peptide-polyester salts of this invention. The peptide-polyester salt is comprised of a hydrophilic peptide, which would prefer thermodynamically to exist or dissolve in an aqueous or polar environment or phase, and a polyester chain which is hydrophobic, and would prefer thermodynamically to dissolve in a hydrophobic phase. That is, the peptide-polyester salt is amphipathic, and has surface-active properties which are not present in simple peptide salts. This surface activity results in the peptide-polyester salt preferring to exist at a phase interface, and because of the general nature of the salt (proportion and length of the hydrophobic chain) the most thermodynamically stable type of dispersion in a largely aqueous phase is for the peptide-polyester salt to exist as a dispersion in water (as the critical micellar concentration is very low, and not all the salt can exist at the interface in many situations.)

It can be seen, therefore, that the peptide-polyester salt is an extremely effective dispersant for making, as well as for maintaining, the stability of aqueous dispersions. In this second procedure for making microparticulate pharmaceutical formulations, the peptide-polyester solution (say, for example, in dichloromethane) is simply dispersed in an aqueous phase, which may optionally contain a viscosity-enhancing polymer such as (but not limited to) polyvinyl alcohol, using the surface-active properties of the peptide-polyester salt. Although some organic solutions containing such peptide-polyester salts may spontaneously disperse, as a general rule some agitation or shear is required in preparing the aqueous dispersion.

A further preferred aspect of the process, as indicated above, is to carry out the operations such that the aqueous dispersion is carried out effectively in the absence of carbon dioxide and in an inert atmosphere. It is further preferred that the organic solution of the peptide-polyester salt be free of carbon dioxide, because the concentration of carbon dioxide in air and water under normal conditions is sufficiently high, in comparison with the concentrations of polyester carboxylic acid groups, to enter into competitive salt formation due to mass action effects, according to the equation:

where P is polyester and D is peptide drug. The resultant aqueous dispersions may then be dried by a variety of techniques, such as removal of the organic solvent in vacuo followed by freeze drying, or by directly removing both the solvent and the water in a single freeze drying operation. The resultant product may then be used to make suitable pharmaceutical preparations for injection in the manner described above.

A further alternative means of making microparticulate pharmaceutical formulations uses an essentially dry solution of the peptide-polyester salt, containing colloidally dispersed free peptide, in a suitable organic solvent or vehicle. (The term "essentially dry" is used, as it is virtually impossible to remove all traces of water from the peptide, and furthermore it means that none of the drug exists as an aqueous solution in a separate aqueous phase.) Addition of a non-solvent for the polymer, under conditions of vigorous agitation, followed by the addition of the solvent-swollen peptide-polyester salt (optionally containing free polymer and optionally containing free drug) to a large volume of a second non-solvent, to further harden and stabilise the precipitated microparticles, gives the final form. Obviously, under the appropriate conditions, or in the presence of a suitable surface active agents, such as (but not limited to) the fatty acid esters of sorbitol, the precipitation of the microparticles can be carried out using a single non-solvent for the polyester, for example a paraffin such as hexane.

The microparticles made by the various processes described herein are totally different structurally from the microcapsules prepared according to the methods outlined in European Patent Nos. 52,510 (Syntex) and 145,240 (Takeda), wherein the peptides are encapsulated in a phase of polyester alone. Microcapsules are defined as one or more cores of one compound or material within a continuous second phase, so that a continuous coating of the second phase material totally encloses or microencapsulates the core material such that none of that material exists at the surface of the microcapsules, and microencapsulated core material retains in all respects the physicochemical and thermodynamic properties of the unencapsulated core compound or material.

Thus, in European Patent No. 52,510, a phase separation coacervation process was used to coat droplets of an aqueous dilute solution of the peptide such that the polymer alone comprised a continuous coating around the aqueous droplets. That is, they are true microcapsules which have the geometry and shape of microspheres. After isolating the precipitated microcapsules and hardening and drying, a product was obtained wherein the peptide drug exists as a discrete core or cores within a polymer envelope. Because of the presence of water in the interior of the microcapsule prior to drying, its removal during the dehydration process at a temperature which is below the glass transition temperature of the polymer can result in a particle which is highly foraminous. At no stage does the process and materials, used or described in European Patent No. 52,510, involve a peptide-polyester salt, nor does the disclosed process allow of sterile filtration of a peptide-polyester solution or suspension, if aseptic manufacture is required.

Furthermore, this prior patent specifically used the polyesters based on lactic and/or glycolic acids described in U.S. Pat. No. 3,773,919 (Boswell), which are defined therein as being benzene-soluble at 25° C. In the present invention, benzene-insoluble polyesters, based on lactic and/or glycolic acids, but which are soluble in chloroform, are preferred for relatively short delivery periods, say less than two months.

In European Patent No. 190,833 (Takeda), the peptide was entrapped as a gelled aqueous solution of drug, and the aqueous gelled phase was dispersed in a polymer solution. This water(aqueous drug gel)-in-oil (polymer solution) dispersion was then itself dispersed under shear in water, to give a water-in-oil-in-water double dispersion. After removal of the organic solvent under vacuum, and lyophilisation, microcapsules were obtained wherein the drug/gelling agent was encapsulated by polymer alone. The products of this process retain the drug as the simple salt, and not as the polymer salt of the peptide. The pharmaceutical formulations of the present invention therefore have structures, physicochemical characteristics and thermodynamic properties, which are totally different from the products described in European Patents Nos. 52,510, 145,240 and 190,833, wherein the microcapsules have the shape and geometry of microspheres in which a core, or cores, of drug is totally enclosed by polymer alone.

The products of this present application can also have the geometry and shape of (but are not limited to) microspheres, but either they are not microcapsules at all as defined above but rather are solutions of peptide-polyester salt (optionally also containing free polymer), or they are microcapsules wherein free peptide drug is encapsulated within a continuous phase or coating of the polymer-drug salt, optionally also containing free polymer. As indicated above, the permeability properties of such a polymer-drug salt are totally different from those of free polymer alone, so the products of the present invention release their peptide drug load in a manner which is totally different from those described in prior European Patents Nos. 52,510, 145,240 and 190,833.

Thus, a further embodiment of the invention is the preparation of either microspheres which are not microcapsules, using a solution of the peptide-polyester salt, optionally containing free polymer, or the preparation of microspheres which are microcapsules, but which comprise free drug encapsulated by a phase or coating of peptide-polyester salt, optionally containing free polymer.

Such diverse particles can be made by a variety of different processes such as precipitation, phase separation coacervation, spray drying and spray congealing. The preferred particle size ranges from 0.2 μm to 500 μm, and said particles can be injected as a suspension in a suitable injection vehicle.

Particularly effective and useful parenteral pharmaceutical formulations of peptide drugs can also be prepared in the form of solutions of a drug-polyester salt, optionally containing free polyester and optionally containing dispersed or solubilised free drug, in a pharmaceutically acceptable organic solvent which is a solvent for the free polyester but a non-solvent for peptides and simple salts thereof, such as for example chlorides and acetates.

Thus, according to the present invention, however, there is provided a pharmaceutical composition comprising a peptide drug and a polyester, for extended release of the peptide drug, characterized in that the composition is in the form of a solution, comprising:

(a) a basic peptide drug, as hereinbefore defined, having a molecular weight of at least 300 Da, and preferably at least 800 Da, which is in the form of a salt with the polyester, the salt comprising a cation of the basic peptide and an anion of a carboxy-terminated polyester, (b) a pharmaceutically acceptable organic solvent which is a solvent for the free polyester but not a solvent for the free peptide, (c) an excess of the polyester, and optionally (d) an excess of the free peptide drug in a solubilised or colloidally dispersed form.

Suitable basic peptides and carboxy-terminated polyesters are those defined above, and particularly preferred peptides are those synthetic LHRH analogues defined above.

For polyester-peptide drug salts wherein the polyester is based on homo- and co-polymers of lactic and glycolic acids, suitable pharmaceutically acceptable organic solvents include, but are not limited to, benzyl benzoate, benzyl alcohol, ethyl lactate, glyceryl triacetate, esters of citric acid, and low molecular weight (<1000) polyethylene glycols, alkoxypolyethylene glycols and polyethylene glycol acetates, etc., and of these benzyl benzoate and benzyl alcohol are preferred, especially benzyl benzoate.

The only requirement for such an organic solvent is that it is pharmaceutically acceptable and that the polyester-peptide drug salt is soluble in it. Whether or not a single such solvent is used, or a mixture of such solvents, the suitability of such solvents can be determined readily by simple experimentation. Homo- and co-polymers of lactic and glycolic acid are amongst the most polar and lipophobic polyesters, and so will not dissolve in such organic injection solvents as ethyl oleate, vegetable oils and other lipophilic carriers, but homo- and co-polymers based on lipophilic monomers or co-monomers, or lipophilic hydroxy acids such as hydroxystearic acid, are soluble in such lipophilic injection vehicles.

The ratio of peptide drug to polyester in the solids which are dissolved to form the solution composition of the invention, will naturally vary according to the potency of the peptide drug, the nature of the polyester used, and the period of peptide drug release desired.

The preferred level of peptide drug incorporation is from 0.1 to 30% w/v. In general, the optimal drug loading is dependent upon the molecular weight of the polyester and its molecular weight distribution, the period of release desired, and the potency of the peptide drug. Obviously, for drugs of relatively low potency, higher levels of incorporation may be required.

Water uptake by the composition is an important factor in controlling the rate of hydrolytic scission of the polyester, and the rate of water uptake is to some degree determined by the drug loading on the composition. Thus, in cases where relatively rapid drug release is required over a relatively short period, say three months, up to 30% peptide drug loading may be appropriate.

The monomer composition of a co-polyester, for example the ratio of lactide to glycolide in lactide-co-glycolide polyesters, is also important in determining the rates of polyester degradation and peptide drug release. Duration of release is also determined in part by the weight average molecular weight of the polyester, but the amount of peptide drug which can be incorporated as drug-polyester salt is determined by the number average molecular weight. That is, polydispersity (the ratio of weight average to number average molecular weights) is an important parameter.

Thus, for durations of peptide drug release of from one to four months, compositions comprising polyesters of weight average molecular weight from 4000 to 20000 with polydispersities of from 1.2 to 2.2, and peptide drug contents of from 0.1 to 30% are preferred. In general, the lower the drug loading, the lower the weight average molecular weight and the higher the polydispersity of the polyester are required. For longer release periods, say from two to six months, it is preferred to use peptide drug loadings of from 0.1 to 20%, and polyesters having weight average molecular weights of 8000 to 20000, and polydispersities of from 1.5 to >2.2. For release periods of greater than six months, peptide drug loadings of from 0.1 to 10% are preferred, suing polyesters having a weight average molecular weight of from 20000 to 50000, and polydispersities of >1.8.

The level of incorporation of total peptide-polyester solids in the composition of the invention will naturally vary, depending upon the potency of the peptide component, the period of time over which delivery of the peptide drug is desired, the solubility of the total solids in the solvent of choice, and the volume and viscosity of the solution composition which it is desired to administer.

The viscosity of the solution composition of the invention is determined by the molecular weight of the polyester and the peptide drug loading. In general, solutions containing over about 40% solids w/v (peptide drug/polyester salt, free drug, free polyester) and where the polyester has a weight average molecular weight of >8000, are difficult to administer by injection because of their viscosity. Thus solutions of ≦40% w/v are preferred for these polyesters. For solution compositions comprising polyesters of weight average molecular weight from about 8000 to about 20000, concentrations of ≦30 w/v are preferred, and for solution compositions comprising polyesters of molecular weight from about 20000 to about 50000, concentrations of ≦20% w/v are preferred. In some circumstances, for example if it is desired to inject the composition using a very narrow needle, very low viscosity solutions may be preferred, and the concentration could be reduced to 2% w/v or even less, but there will be a balance, of course, between reducing the viscosity and increasing the volume required to be injected.

According to a further feature of the invention, there is provided a process for the manufacture of a composition of the invention, which comprises:

1. dissolving an intimate mixture of the basic peptide drug and the polyester in the pharmaceutically acceptable solvent; or
2. slowly adding a solution of the peptide drug in a 1–6C alkanol to a solution of the polyester in a solvent suitable for injection, whereafter if the hydroxylic solvent is not pharmaceutically acceptable for injection it is removed by evaporation, or if the hydroxylic solvent is pharmaceutically acceptable for injection, its removal may not be necessary.

The intimate mixture of the basic peptide drug and the polyester, used in process 1. above, is preferably obtained by dissolving the basic peptide and the polyester in a solvent or solvent mixture which is capable of dissolving both the basic peptide drug and the polyester, and which is capable of being freeze-dried. Suitable examples of such solvents or solvent mixtures are glacial acetic acid and mixtures of dioxan and water, followed by freeze drying of the solution so obtained. Alternatively, the two components may be dissolved in for example dimethylsulfoxide, and the solvent subsequently removed.

The intimate mixture may also be obtained by dissolving the peptide drug in a hydroxylic solvent, for example methanol, and adding this solution to a solution of the polyester in for example dichloromethane, followed by removal of the solvents, for example by evaporation.

Alternatively, an aqueous solution of the peptide drug as the chloride salt may be added to an aqueous solution or dispersion of the sodium salt of the polyester, and the mixture freeze dried to give a mixture of the peptide drug/polyester salt and sodium chloride. The latter may be removed if desried by mixing the product in an organic solvent and filtering off the insoluble sodium chloride.

In process 1. dissolution of the intimate mixture in the pharmaceutically acceptable solvent may be hastened by heating and/or stirring of the reaction mixture.

In process 2. above, a suitable alkanol solvent for the peptide is for example, methanol, ethanol or propylene-1,2-diol.

A major advantage of pharmaceutical peptide drug products in the form of solutions of a polyester-peptide drug salt, optionally containing free drug and/or free polyester, is that preparation of an injectable product in sterile form, for immediate use without any need for premixing prior to administration to a patient, can be manufactured using sterile filtration. This is a much simpler manufacturing operation than the sterilisation of a solid or suspension product. An alternative process for the manufacture of sterile injectable solutions is to dissolve a sterile polyester-peptide drug salt, optionally containing free drug and/or free polyester, in the pharmaceutically acceptable organic injection vehicle.

Although these formulations are primarily those for parenteral routes of administration, the polyester-drug salts of the invention may also be used in the manufacture of orally administrable formulations.

A quite different type of formulation, which can be injected or implanted sub-dermally, is a drug delivery system based on implants or mixtures of different types of implant. These can be prepared from the polyester-peptide drug salts of the invention, optionally containing free drug and/or free polyester, using conventional polymer melt-processing techniques, such as, but not limited to, extrusion, and compression and injection moulding, wherein elevated temperatures (preferably less than 100° C.) are used to melt the polyester-drug salt in the preparation of the implant. Preparations of such implants can be carried out under aseptic conditions, or alternatively by terminal sterilisation by irradiation, using but not limited to γ- or X-rays. These solid dosage forms can be reduced to microparticulate forms by comminution or milling. The preferred particle sizes may range from 1 μm to 500 μm, and these microparticle delivery systems (which are neither microspheres nor microcapsules) can be suspended in a suitable conventional pharmaceutically acceptable injection vehicle.

The melt-processing of the peptide-polyester drug salt embodies and illustrates a most significant and important difference between the physicochemical and thermodynamic properties of the peptide-polyester drug salts of this invention, and the free peptides and simple salts thereof. The peptide-polyester salts of this invention in many instances melt and flow, in contrast to the free peptides and their simple salts, such as chlorides and acetates, which do not melt, but decompose at elevated temperature.

Degradation of polyesters is in part dependent on their molecular weight and polydispersity. Obviously, for degradation to occur mainly by hydrolytic scission of ester groups, the polyester or a pharmaceutical formulation containing a polyester, must take up water. For those systems where the release controlling matrix or membrane contains, in whole or in part, peptide-polyester drug salt, there will be a higher water uptake by the controlling matrix or membrane when compared to the polyester alone. Consequently, continuous matrix phases or membranes containing polyester-drug salt degrade differently from those continuous matrix phases or membranes based on polyester alone. It will also be understood that the rate of diffusion of water or physiological fluids into such a release controlling polyester matrix or membrane will control in part the rate of degradation. This diffusion of water or physiological fluids is also governed by the dimensions and shape of the formulation, and so drug release from compositions containing polymeric salts of polypeptides and polyesters is also dependent on these factors.

Of particular interest as the polyester component of the peptide-polyester drug salts of this invention, are those based on homo- and co-polymers of lactic and glycolic acids, wherein the lactic may be in any one or more of its optically active and racemic forms. Polyesters of this general type have been known for many years and have been studied in detail in a variety of controlled release drug delivery systems (see, for example, "Controlled Release of Bioactive Agents from Lactide/Glycolide Polymers", by D H Lewis in "Biodegradable Polymers as Drug Delivery Systems", ed. M Chasin & R Langer, Marcel Dekker, and references therein).

For example, U.S. Pat. No. 3,773,919 indicates in broad general terms that controlled release pharmaceutical formulations of lactide polyesters and lactide co-polyesters containing antimicrobial polypeptides might be prepared. However, the antimicrobial peptides disclosed therein are unsatisfactory for generating a polyester salt, since they either occur as sulfates, or have other features which inhibit or prevent the formation of a polyester-peptide drug salt. Indeed, when the Examples shown in this patent are followed, the mixing of the peptide drug, irrespective of its nature, with a polymer at an elevated temperature as disclosed, results in catastrophic decomposition of the peptide drug.

Similarly, an antimicrobial polypeptide, colistin, is disclosed in European Patent No. 25,698 as one of many listed compounds which allegedly may be formulated with polylactide, but once again this compound has structural features which prevent salt formation with the terminal carboxylic acid groups of the polyester. Colistin is used pharmaceutically only as colistin sulfate or colistin sulfomethate sodium, neither of which forms allows the manufacture of amphipathic salts with polyesters according to the present invention. Other prior art which discloses the use of polypeptides with biodegradable polymers based on homo- and co-polymers of lactic and glycolic acids are European Patents Nos. 52,510, 58,481, 145,240 and 190,833, previously referred to above.

Although co-polymers of lactic and glycolic acids have been known for many years, the complexity of their structure with regard to the distribution of the co-monomer units and their subsequent sequence length (runs of the same individual co-monomer unit in the co-polymer, which are other than random), and the effect of such structural variations when used as drug release matrixes, have largely been ignored in the prior art. This co-polymer structure determines, in part, both the solubility or swellability of the polymer in solvents such as benzene, as well as the rate of degradation. This correlation was first noted by Hutchinson (European Patent No. 58,481), but has been extended and refined in the present invention.

To illustrate this point, U.S. Pat. No. 3,773,919 discloses certain controlled release drug formulations using 50/50 co-polyesters of lactic and glycolic acids which are soluble in benzene, and indeed this U.S. patent is specifically limited (in respect of lactic/glycolic copolymers) to those which are benzene-soluble. The utility of these benzene-soluble co-polyesters has been further reinforced by their specific use in European Patent No. 52,510. However, earlier U.S. Pat. No. 2,703,316, (which was commonly owned with U.S. Pat. No. 3,773,919) disclosed 50/50 lactide/glycolide co-polyesters which were insoluble in benzene. Since these two U.S. patents were commonly owned (duPont), it must be assumed that, in the invention claimed in the later of these patents, the benzene-insoluble co-polymers were inferior in some respect as compared to those which were benzene-soluble. This view is reinforced by European Patent No. 52,510, which used only the benzene-soluble co-polymers of U.S. Pat. No. 3,773,919.

The prior art, with the exception of our own European Patent No. 58,481, has ignored the effect which the structure of co-polyesters of lactic and glycolic acids has on their solubility and degradability. We have shown that for polyesters of similar molecular weight and molecular weight distribution the following general relationship applies in most cases for polyesters which are soluble in chloroform at 25° C., namely benzene-insoluble polyesters degrade faster than polyesters which are swollen but not dissolved by benzene, and such benzene-swellable polyesters degrade faster than those polyesters which are freely soluble in benzene, when degradation experiments are carried out in aqueous physiological fluids, or in buffer at pH 7.4 at 37° C. Consequently, it is particularly useful to use polyesters which are insoluble in benzene to provide continuous release of peptides from parenteral formulations over a relatively short period of time, say from one week to two months.

Thus, for compositions which may contain from 0.1% w/v of peptide up to 75% w/v of peptide, the following holds with respect to polyester composition, and its relations to structure, viscosity and polydispersity.

For the manufacture of peptide-polyester drug salts which can be formulated in accordance with this invention to give continuous drug release over a period of a week to two months, the molar composition of such benzene-insoluble polyesters, which preferably have a normal to wide polydispersity, preferably ranges from 60% glycolic acid (or glycolide)/40% lactic acid (or lactide) to about 25% glycolic acid (or glycolide)/75% lactic acid (or lactide), and such polyesters preferably have an inherent viscosity at 1% w/v in chloroform at 25° C. ranging from 0.08 to 4.0 dl/g.

By suitable choice of the polyester parameters, including molecular weight and molecular weight distribution, it is also possible to achieve continuous release of polypeptides over a period of one week to two months from formulations according to this invention, using polylactic acid homopolymer or co-polyesters having a molar composition ranging from 35% glycolic acid (or glycolide)/65% lactic acid (or lactide) to 10% glycolic acid (or glycolide)/90% lactic acid (or lactide), which are soluble in benzene, have an inherent viscosity at 1% in chloroform at 25° of from 0.08 to 0.5 dl/g, and have a narrow to wide polydispersity.

Continuous release of peptides over a relatively longer period of time, say 2 to 6 months, from formulations according to this invention, may be achieved using polylactic acid homopolymer or co-polyesters having a molar composition ranging from 35% glycolic acid (or glycolide)/65% lactic acid (or lactide) to 0% glycolic acid (or glycolide)/100% lactic acid (or lactide), which are benzene-soluble, have an inherent viscosity at 1% w/v in chloroform at 25° C. of from 0.08 to 0.8 dl/g, and have a narrow to wide polydispersity.

Continuous release of peptides over a very long period of time, say up to 2 years, from formulations according to this invention, may be achieved using polylactic acid homopolymer or co-polyesters having a molar composition ranging from 25% glycolic acid (or glycolide)/75% lactic acid (or lactide) to 0% glycolic acid (or glycolide)/100% lactic acid (or lactide), which are benzene-soluble, have an inherent viscosity at 1% w/v in chloroform at 25° C. of from 0.2 to 4.0 dl/g, and a normal to high polydispersity.

Timed or pulsed release (with an induction period prior to release), or discontinuous release (where there is an initial phase of release followed by a period of no release or ineffective release, followed by a second phase of release), over a relatively short period of time, say up to 2 months, may be acheived with the formulation according to this invention, using benzene-insoluble polymers which have a narrow to most-probable molecular weight distribution, and an inherent viscosity at 1% w/v in chloroform at 25° C. from 0.3 to 4.0 dl/g.

Yet another feature of the present invention, which is novel and distinguishes this invention from all other previously described controlled release drug delivery system based on polyesters or co-polyesters, and which further controls the rate of release, is the level of incorporation of peptide as the polyester salt (optionally in the presence of free drug and/or free polymer). This further controlling feature differs entirely from those parameters which result in increased release rates in more conventional delivery systems based on polyesters, which are directed towards the delivery of highly lipophilic drugs having relatively low aqueous solubility, such as steroids. In those cases, as the level of drug incorporation increases, an increased rate of release is generally seen, even though the water uptake of such systems is reduced, due to the increased phase volume of lipophilic drug. In fact, such increased rates of release of drugs such as steroids are dependent on the drug retaining its thermodynamic identity, and on simple Fickian diffusion kinetics (see Baker and Lonsdale, loc. cit.) That is, for drugs such as steroids, as drug loading increases, and providing the lipophilic drug has some solubility in the lipophilic polymer, simple Fickian diffusion rates are increased.

A totally different situation exists, however, with the products of the present invention. It is now recognised that a major component part of the degradation of polyesters and co-polyesters is hydrolysis of ester groups, and the rate at which this occurs is dependent on water uptake (see Pitt and Zhong-wei Gu, J. Controlled Release, 4, 283–292 (1987); Hutchinson and Furr, ibid., 13, 279–294 (1990)). Peptides are hydrophilic, and their salt formation with polyesters results in a phase containing polyester-drug salt which has a higher water uptake than the polyester alone. That is, the polyester chain in the salt can degrade faster than free polyester alone, which has a similar composition, molecular weight and polydispersity. As peptide release is strongly dependent on degradation, then release is governed in part by both the level of incorporation of the polyester-peptide drug salt in the composition, and the proportion of peptide in the salt. For polyesters or co-polyesters of the same composition and structure, increasing one or both of these parameters results in increased rates of release, and by implication can reduce, in certain circumstances, the periods of time over which release can occur. Levels of peptide drug incorporation, either as polyester-drug salt, or as polyester-drug salt in combination with free peptide, preferably range from 0.1% w/w to 75% w/w in the polyester-drug formulation.

The peptide drug loading in the composition of the invention and its variation with polyester molecular weight and polydispersity, is as follows. For continuous release of a peptide over very long periods of time, say up to 2 years, low levels of drug incorporation, ranging from 1.0% to 20% w/w, are preferred, using polyesters which have a preferred weight average molecular weight of 20,000 Da or more and polydispersities greater than 2.2 and preferably greater than 3.5. These parameters for very long term release also depend in part on other features within the drug formulation, such as composition with respect to co-monomer content, structure, solubility/insolubility in benzene, and geometry and dimensions of the dosage form. A polyester of weight average molecular weight of about 20000 has an inherent viscosity of about 0.2, dependent upon such factors as its structure, composition and polydispersity.

For continuous release over relatively long periods of time, say up to 6 months, preferred levels of peptide drug incorporation range from 0.5% to 35% w/w, using polyesters or co-polyesters having weight average molecular weights of preferably 10,000 Da or more, and polydispersities greater than 1.8 and preferably greater than 2.2, depending on all other parameters such as composition, structure, solubility/insolubility in benzene, and geometry and dimensions of the dosage forms.

For continuous release over relatively short periods of time, say up to 2 months, preferred levels of peptide drug incorporation range from 0.1% to 75% w/w, using polyesters having preferred weight average molecular weights of 2,000 Da or more, and polydispersities greater than 1.2, depending on all other parameters such as composition, structure, solubility/insolubility in benzene, and geometry and dimensions of the dosage forms.

An additional parameter which further controls peptide drug release from formulations according to this invention, and which is absent from prior art types of delivery systems based on homo- and co-polymers of lactic acid and glycolic acid, is the functionality of the peptide, with regard to the number of basic groups such as arginine and lysine residues in the peptide drug molecule, and the functionality of the polyester or co-polyester with respect to the average number of carboxylic acid groups contained by the average polymer or co-polymer chain. In general, for continuous release of the peptide drug, the greater the level of such polyfunctional interaction in the peptide-polyester polyelectrolyte complex, the greater the polydispersity required. In contrast, for discontinuous or pulsed release, polydispersities of less than 2.2 are preferred.

One of the relatively rare occurrences of mutual compatibility or solubility of two polymer types having different chemical structures, is represented by mixtures of polyesters, based on homo- and co-polymers of lactic and glycolic acids, with low molecular weight polyoxyethylenes, and in particular low molecular weight polyethylene glycols. This compatibility has been put to good effect in polyester-peptide drug salts and their preparation, in the present invention, in a novel and unexpected way. Thus, it is known that certain pharmacologically active peptides can be 'pegylated', that is conjugated with a polyethylene glycol or alkoxy-polyethylene glycol, in such a way that the pharmacological activity of the peptide is retained. The presence in the pegylated peptide molecule of the conjugated polyoxyethylene chain thus renders the pegylated peptide partially compatible with the polyester or co-polyester.

Thus, providing that the remaining lysine or arginine residues in the pegylated peptide occur as salts of weak acids, this compatibility facilitates the preparation of the polyester-peptide drug salt, as well as adding a further element of control of release. Pharmacologically active conjugates of peptides with other water-soluble polymers, such as polysaccharides, synthetic polypeptides and polyvinyl pyrrolidone, are also useful, but are less preferred as none of these latter water-soluble polymers is soluble or compatible with the polyester or co-polyester.

This invention preferably applies to pharmacologically active drugs containing basic functionality. However, it can also be applied to peptides which are pharmacologically active and which are either neutral or tend to exist largely as polyanions (polypeptides having excess carboxylic acid functionality).

In the first of these instances (a pharmacologically active neutral polypeptide containing neither acidic nor basic residues) a salt of a synthetic polypeptide, which contains basic functionality and which is pharmacologically inactive, and the polyester, is used. Such a salt of the pharmacologically inactive synthetic polypeptide and the polyester or co-polyester is also amphipathic, and so can act as a dispersing agent for solubilising or colloidally dispersing a pharmacologically active, but neutral, peptide in an organic phase.

In the second of these cases, (where the pharmacologically active polypeptide contains residual carboxylic acid functionality), a salt of a synthetic polypeptide having at least two basic groups in the synthetic polypeptide chain, and which is pharmacologically inactive, and a polyester or co-polyester, is used. In this second case, in the salt of the synthetic polypeptide and polyester, the concentration of basic functional groups in the salt is greater than the concentration of carboxylic acid groups in the acidic, pharmacologically active peptide. This excess basic functionality in the salt can then interact by further salt formation with the carboxylic acid groups of the acidic pharmacologically active peptide. The resulting salts complex may then be solubilised or dispersed in an organic solvent or phase which is normally a total non-solvent for the peptide in question, but which are solvents for the polyester or co-polyester, in the manner described above for other polyester-peptide salts.

Because salts of peptides containing basic functionality with polyesters and co-polyesters containing carboxylic acid functionality are amphipathic, their surface active properties can be used to facilitate the dispersion of other hydrophilic drugs, or aqueous suspensions of such drugs, in an organic solvent or phase containing the polyester-peptide salt. The use of such amphipathic salts of peptides with polyesters or co-polyesters as dispersing or solubilising agents forms a further feature of this invention.

The invention is illustrated, but not limited, by the following Examples.

The measurement of viscosities and their relationship to the various averaged molecular weights are discussed in Sorensen and Campbell, "Preparative Methods of Polymer Chemistry", 2nd edition, 1968, Interscience Division of John Wiley, pages 43–50. In the Examples described below herein, an Ubbelohde viscometer giving a flow time for chloroform alone of about 100 seconds was used. Chloroform was used as the solvent as this was a solvent for both benzene-soluble and benzene-insoluble polymers over the composition range disclosed.

Molecular weights and molecular weight distributions of polyesters described in this application of molecular weight greater than about 2000 Da, were determined by size exclusion chromatography, relative to polystyrene standards, using 3×30 cm PL Gel, 10 μm mixed B columns (ex Polymer Laboratories, Church Stretton, Shropshire, UK) connected in series and fitted with a 10 μm guard column. Tetrahydrofuran was used as solvent at 40° C. with a nominal flow rate of 1 ml per minute. Molecular weight characteristics were calculated using Data Analysis Package Perkin-Elmer 7700 Professional Computer with GPC software.

For measurement of molecular weights of less than 2000 Da, size exclusion chromatography is not the preferred method of molecular weight determination, and instead non-aqueous potentiometric titration can be used, to give either the molecular weight or equivalent weight of the polyester, by direct measurement of the carboxylic acid content of the polyester or co-polyester. Non-aqueous potentiometric titrations were generally carried out using a known weight of polyester or co-polyester dissolved in acetone containing 10% v/v of water. Titrations were carried out using dilute sodium hydroxide solutions and using equipment supplied by Radiometer (Copenhagen, Denmark). This consisted of a titrator (TTT 80) and autoburette (ABU 80), a pH meter (PHM 83) and a Russell CMAWK electrode. The titration was plotted on a Servograph (REC 80) and molecular weight of the polymer is $$\frac{w \times 1000 \times f}{v \times n}$$

where w is the weight of polymer used, f is the average number of carboxylic acid groups per polymer chain v is the volume of sodium hydroxide used, n is the normality of the sodium hydroxide used.

EXAMPLE 1

Goserelin acetate (100.6 mg, equivalent to about 86 mg of peptide as free base), and 50/50% molar D,L-lactide/glycolide co-polymer (300.3 mg) containing one terminal carboxylic acid group per polymer chain and having a weight average molecular weight of 4300 Da and an inherent viscosity at 1% w/v in chloroform at 25° C. of 0.08 dl/g, and which was insoluble in benzene, were dissolved in anhydride-free glacial acetic acid (3 ml). The acetic acid solution of drug and polymer was added dropwise to liquid nitrogen, and the frozen droplets were freeze-dried for 24 hours under high vacuum conditions. The freeze-dried product was finally post-dried at 50° C. for 24 hours under high vacuum, to give a polyester-drug mixture containing nominally about 25% w/w goserelin acetate (equivalent to about 22.3% w/w peptide as free base).

The dried polyester-drug mixture (400 mg) was added to dichloromethane, and made up to 4 ml. Initially, a cloudy colloidal mixture was obtained, but over the course of 1 hour this gradually cleared to form a clear solution. This solution was cast as a film, and allowed to dry at room temperature for about 6 hours, then for 20 hours at 50° C. under high vacuum. A clear, transparent film containing polyester-drug salt was thus obtained.

(i) The clear, transparent film (100 mg) thus obtained was melted and compression moulded at 80° C. to give a transparent film, about 0.02 cm thick. On immersion in water at 37° C. for 24 hours, the weight of the hydrated drug/polymer film increased to 225 mg. In contrast, the polyester alone (100 mg) similarly treated increased in weight to only 126 mg, and a film comprising a simple admixture of goserelin acetate (25 mg) and polymer (75 mg) (made by adding drug to a solution of polymer in dichloromethane, removing the solvent and compression moulding the resulting material to give film about 0.02 cm thick) weighed only 136 mg after 24 hours immersion in water at 37° C. It is apparent from this experiment that the polyester-drug salt composition is considerably more hydrophilic, and has a higher water-uptake, than either the polyester alone or simple admixtures of drug and polyester.

In the simple admixture of drug and polymer in dichloromethane, the drug showed no sign of dissolving even after 1 month, and when dried and compression moulded, the simple admixture gave an opaque film. However, in a further experiment, the clear, transparent film obtained above (100 mg) was dissolved in dichloromethane (1 ml) to give a clear, transparent polyester-drug solution. To this solution was added trifluoroacetic acid (50 μl), and the mixture was stirred vigorously. There was an immediate precipitate of goserelin as the trifluoroacetate salt.

These two experiments show that the clear, transparent film containing polyester-drug salt, obtained as described above, is capable of being processed to a shaped delivery system using conventional polymer melt fabrication techniques. Further, this product contains virtually no acetic acid or acetate anion, and so the drug must exist in the form of the polyester salt. The polyester-drug salt arises because the terminal lactic or glycolic acid groups on the co-polymer are much stronger acids than acetic acid, and so the weaker acetic acid is displaced by the polymer. The polymer carboxylic acid in the dichloromethane-soluble polyester-drug salt can in turn be displaced by a very much stronger carboxylic acid, such as trifluoroacetic acid. When this occurs, the trifluoroacetate salt of the peptide is formed and, as it is not soluble in dichloromethane, is precipitated.

(ii) The clear, transparent film obtained as described above (50 mg), containing the polyester-drug salt, was moulded to give a film about 0.02 cm thick. The film was incubated in phosphate buffered saline (containing 0.02% sodium azide) at pH 7.4 and 37° C., and the buffer solution was assayed periodically by UV to determine the amount of goserelin released. This moulded product released goserelin continuously over about 2 weeks, and by 3 weeks had virtually degraded completely, and disappeared from the incubation medium.

This experiment demonstrates the utility of very low molecular weight, benzene-insoluble polymers for delivery of drug over a short time interval.

Similar moulded formulations can be manufactured using, in place of goserelin acetate, either naturally occuring gonadotrophin releasing hormones or other highly potent synthetic analogues (agonistic or antagonistic) of gonadotrophin releasing hormone, such as tryptorelin, leuprorelin, buserelin and nafarelin, preferably as the acetate salts or salts with other weak acids; or any other polypeptide hormone which controls secretion of the intact gonadotrophin or either of the gonadotrophin subunits.

EXAMPLE 2

The clear, transparent film product obtained in Example 1 above (100 mg) and a 50/50 molar D,L-lactide/glycolide co-polymer (1.05 g) having a weight average molecular weight of 121,000 Da and an inherent viscosity at 1% w/v in chloroform at 25° C. of 0.84 dl/g, and which is insoluble in benzene, were dissolved in dichloromethane (100 ml). The solution was stirred vigorously at 1000 revolutions per minute (rpm), and silicone oil (50 ml) was added slowly over 1 hour, to precipitate both the polyester-drug salt and the free polyester. After 1 hour, the partially precipitated mixture of polyester-drug salt, free polyester, silicone oil and dichloromethane was added to vigorously stirred hexane (2 litres) to harden the microparticles of polyester-drug salt and free polyester. This mixture was stirred for 2 hours and then allowed to settle, and the hexane layer was discarded. The microparticles (containing about 1.95% w/w goserelin as free base) were washed three times with fresh hexane (500 ml), and finally isolated by filtration and dried at 35° C. for 24 hours under high vacuum. The average size of the approximately spherical microparticles so obtained, which comprise a solution of polyester-drug salt in free polymer, was about 30 μm.

A portion of this product (250 mg) was incubated in phosphate-buffered saline (containing 0.02% sodium azide) at pH 7.4 and 37° C., and the buffer solution was assayed periodically by UV to determine the amount of goserelin released. The microparticles released drug over about 5 weeks, and by 7 weeks had virtually disappeared from the incubation medium.

The polymer composition used in this experiment was a mixture of two co-polymers of the same lactide/glycolide composition, but having widely different molecular weights, and which as a mixture, as described here, was insoluble in benzene, had a weight average molecular weight of 108,000 Da, a polydispersity of 5.1, and an inherent viscosity at 1% w/v in chloroform at 25° C. of 0.72 dl/g.

These experiments show the utility of benzene-insoluble polyesters having a high molecular weight and a high polydispersity, for release of goserelin over relatively short periods of time of 5–7 weeks.

Similar microparticle formulations can be manufactured using, in place of goserelin acetate, either naturally occurring analogues of gonadotrophin releasing hormones or other highly potent synthetic analogues (agonists or antagonists) of gonadotrophin releasing hormone, such as tryptorelin, leuprorelin, buserelin or nafarelin, preferably as the acetate salts or salts with other weak acids; or any other polypeptide hormone which controls or modulates secretion of the intact gonadotrophins or either of the individual gonadotrophin sub-units.

EXAMPLE 3

Goserelin acetate (101 mg, equivalent to about 86 mg of goserelin as free base) and a 100% molar poly(D,L-lactic acid), (299.7 mg), which was soluble in benzene, had a weight average molecular weight of about 5400 Da, an inherent viscosity at 1% w/v in chloroform at 25° C. of 0.08 dl/g, and a polydispersity of 1.8, were dissolved in anhydride-free glacial acetic acid (4 ml). This acetic acid solution of goserelin and polyester was added dropwise to liquid nitrogen, and the frozen droplets were isolated, freeze-dried under vacuum for 24 hours, and then dried at 55° C. for 24 hours under high vacuum.

(i) The resulting dried product was added to dichloromethane (4 ml), to give a cloudy mixture initially, which rapidly dissolved to give a clear solution which was filtered through a 0.2 μm nylon sterilising filter.

This experiment shows that solutions of the polyester salt of goserelin can be sterile-filtered, in contrast to mixtures or dispersions of simple drug salts in an organic solution of the polyester.

(ii) Trifluoroacetic acid (50 μl) was added to the clear dichloromethane solution from (i) above (1 ml), with vigorous agitation. There was an immediate precipitation of goserelin as its trifluoroacetate salt, showing that the goserelin was present in the dichloromethane solution as the salt with the carboxy-terminated polyester.

Similar sterile solution formulations can be manufactured using, in place of goserelin acetate, either naturally occurring gonadotrophin releasing hormones or other highly potent synthetic analogues (agonistic or antagonistic) of gonadotrophin releasing hormone, such as tryptorelin, leuprorelin, buserelin or nafarelin, preferably as the acetate salts or salts with other weak acids; or any other polypeptide hormone which controls or modulates secretion of the intact gonadotrophins or either of the individual gonadotrophin sub-units.

EXAMPLE 4

The dichloromethane solution of goserelin-polyester obtained in Example 3 (2 ml) was diluted with more dichloromethane and made up to 10 ml. This solution was sprayed into vigorously stirred hexane (1 litre), to give microparticles which, after isolation and drying under vacuum at 45° C. for 24 hours, ranged in size from about 2 $\mu$m to about 30m, with an average size of about 10 $\mu$m. The goserelin content of these microparticles was equivalent to about 22% as free base.

These microparticles were incubated in saline, buffered with phosphate to pH 7.4 at 37° C., and the supernatant periodically assayed by UV for goserelin. Goserelin was released continuously, the release was essentially complete by about 8 weeks, and by 11 weeks the microparticles had totally degraded and disappeared from the incubation medium. This experiment shows the utility of very low molecular weight benzene-soluble polyesters in providing continuous peptide release over about 2 months.

If the goserelin acetate in the above experiments is replaced by the trifluoroacetate salt, then a clear solution is not obtained, but instead the polyester solution in dichloromethane contains essentially a dispersion of goserelin trifluoroacetate. This mixture will not pass through a 0.2 $\mu$m filter, and so is not capable of being sterile-filtered; and such a dispersion of goserelin trifluoroacetate in the polyester solution, when sprayed into stirred hexane produced a congealed and flocculated mass, rather than microparticles.

Thus the goserelin-polyester salt has properties which render it much easier to formulate into a microparticle form, than mixtures of the simple salt in a solution of very low molecular weight polymer.

Similar microparticle formulations may be manufactured by using, in place of goserelin acetate, either naturally occurring gonadotrophin releasing hormones or other highly potent synthetic analogues (agonists or antagonists) of gonadotrophin releasing hormone, such as tryptorelin, leuprorelin, buserelin or nafarelin, preferably as the acetate salts or salts with other weak acids; or any other polypeptide hormone which controls or modulates secretion of the intact gonadotrophins or either of the individual gonadotrophin sub-units.

EXAMPLE 5

Goserelin acetate (304 mg, equivalent to about 248 mg of goserelin as free base) and 100% molar poly(D,L-lactic acid) (102 mg), having a weight average molecular weight of about 5400, an inherent viscosity at 1% w/v in chloroform at 25° C. of 0.08 dl/g, and a polydispersity of 1.8, were dissolved in anhydride-free glacial acetic acid (2 ml). The acetic acid solution of goserelin and polyester was then added dropwise to liquid nitrogen, and the frozen droplets were isolated, freeze-dried under high vacuum for 24 hours, and then dried under vacuum at 55° C. for 24 hours.

The resulting product was added to dichloromethane (2 ml) to give a cloudy, colloidal mixture which did not clear totally with time. This mixture in dichloromethane comprised essentially a dispersion of goserelin acetate in the goserelin-polyester salt.

This dispersion of goserelin acetate in the methylene chloride solution of the polyester-goserelin salt was formulated into a microparticulate form, containing goserelin equivalent to about 72% w/w as free base, wherein the free goserelin acetate is dispersed throughout a continuous phase of the goserelin-polyester salt, by spray drying, spray-congealing, simple precipitation or by phase separation co-acervation.

Similar microparticle formulations may be manufactured by using, in place of goserelin acetate, either naturally occuring gonadotrophin releasing hormones or other highly potent synthetic analogues (agonists or antagonists) of gonadotrophin releasing hormones, such as tryptorelin, leuprorelin, buserelin or nafarelin, preferably as the acetate salts or salts with other weak acids; or any other polypeptide hormone which controls or modulates secretion of the intact gonadotrophins or either of its individual sub-units.

EXAMPLE 6

A co-polyester of D,L-lactic acid and glycolic acid, having a molar composition of 78% D,L-lactic acid and 22% glycolic acid, was prepared by co-polycondensation of the two hydroxy acids. After purification of the co-polymer, by addition of a solution of the co-polyester in acetone to methanol to precipitate the co-polyester, and separation and drying the precipitated material, the co-polyester had a weight average molecular weight of about 11,000 Da, a number average molecular weight (as determined by non-aqueous potentiometric titration and assuming that each co-polyester chain has only one terminal carboxylic acid group) of 6100 Da, and therefore a polydispersity of 1.6, and an inherent viscosity at 1% w/v in chloroform at 25° C. of 0.15 dl/g.

Goserelin acetate (228.9 mg, equivalent to about 200 mg of goserelin as free base) and the above-described co-polyester (1.8 g) were dissolved in anhydride-free glacial acetic acid (10 ml). The goserelin-polyester solution so obtained was added dropwise to liquid nitrogen, and the frozen droplets were isolated, freeze-dried for 24 hours, and then finally dried at 50° C. for 24 hours under vacuum.

The dried goserelin-polyester mixture was added to dichloromethane (10 ml) to give initially a cloudy colloidal mixture, but after 24 hours this had changed to a clear solution, which could be filtered through a 0.2 $\mu$m nylon sterilising filter.

When trifluoroacetic acid was added to a small aliquot of this clear solution, there was an immediate precipitate of the goserelin as its trifluoroacetate salt, showing that, in the clear, transparent dichloromethane solution, the goserelin in the goserelin-polyester mixture was present mainly or wholly as the polyester salt.

The dichloromethane solution of the goserelin-polyester salt was evaporated to dryness, and the resulting solid was dried at room temperature for 6 hours and then at 55° C. for 20 hours under vacuum, to give a clear cast film containing goserelin-polyester salt.

The dried goserelin-polyester mixture, prepared as described above, (1 g) was dissolved in 8 ml of dichloromethane. The resulting solution was placed in a 250 ml multinecked round-bottomed flask and swept with a stream of nitrogen to remove all air, and to generate a carbon dioxide-free atmosphere. Water (90 ml), which had previously been degassed to remove all carbon dioxide and then stored under carbon dioxide-free nitrogen, was introduced into the flask, and the mixture was stirred vigorously at about 500 rpm under an atmosphere which was essentially carbon dioxide-free. The dichloromethane solution of goserelin-polyester salt rapidly dispersed to give a stable oil (dichloromethane solution of drug-polymer salt)-in-water dispersion. Whilst maintaining stirring at about 200 rpm, a vacuum was gradually applied and the bulk of the dichloromethane was evaporated under vacuum, to give a dispersion of goserelin-polyester salt in water. Freeze-drying this dispersion produced microparticles, in which the goserelin is present as the goserelin-polyester salt having an average particle size of about 20 μm, which was shown to release goserelin over about 6 weeks, when incubated in saline, buffered with phosphate to pH 7.4 at 37° C., and the supernatant periodically assayed by UV for goserelin.

Similar microparticles may also be manufactured by incorporating in the aqueous phase agents which are known to improve polypeptide stability such as mannitol. Although it is preferred to carry out the above process in a carbon dioxide-free atmosphere, it is nevertheless possible to achieve satisfactory results in the presence of traces of carbon dioxide, depending on polyester molecular weight and drug loading.

Similar sterile solution, cast film and microparticle formulations may be manufactured in a similar manner using, in place of goserelin acetate, either the natural analogues of gonadotrophin releasing hormones or other highly potent synthetic analogues (agonists or antagonists) such as tryptorelin, leuprorelin, buserelin or nafarelin, preferably as acetate salts or salts with other weak acids; or any other polypeptide hormone which can control or modulate the secretion of intact gonadotrophins or either of their sub-units.

EXAMPLE 7

The procedure described in Example 6 was repeated, to give the clear transparent film, and this film (1 g) was dissolved in dichloromethane (4 ml). The solution was warmed to about 35° C., and then an aqueous solution, at about 40° C., of purified gelatin (15 mg) in water (100 μl) was added to the dichloromethane solution of goserelin-polyester salt, and the mixture was stirred vigorously at about 35° C. to give an extremely fine dispersion of the aqueous gelatin solution in the dichloromethane solution of the goserelin-polyester salt. On cooling to room temperature, the colloidal nature of the suspension was maintained.

This experiment demonstrates that the goserelin-polyester salt has surface active properties, and can be used to give stable dispersions in an oily phase, such as dichloromethane, of aqueous solutions of other water-soluble agents, such as gelatin, polysaccharides and other hydrophilic polymers, or vice versa.

The process described in Example 6 was repeated, using the dispersion of aqueous gelatin in the dichloromethane solution of the goserelin-polyester salt described above, to give a microcapsule product which contains both gelatin and goserelin-polyester salt.

Other low molecular weight compounds may be incorporated in the aqueous polymer phase. In particular, it is sometimes useful to include compounds such as mannitol, which are known to enhance the stability of peptides. Alternatively, these stabilising agents may be incorporated in both aqueous phases of the complex water-in-oil-in-water dispersion, comprising aqueous gelatin dispersed in the dichloromethane solution of the goserelin-polyester salt, and the resulting water-in-oil dispersion in turn is dispersed in water.

Similar suspension and microparticle formulations may be manufactured similarly using, in place of goserelin acetate, other highly potent analogues (agonists or antagonists) of gonadotrophin releasing hormone, such as tryptorelin, leuprorelin, buserelin or naferelin, preferably as the acetate salts or salts with other weak acids; or any other polypeptide hormone which can control or modulate the secretion of intact gonadotrophins or either of their sub-units.

EXAMPLE 8

Goserelin acetate (771 mg, equivalent to about 670 mg of goserelin as free base), 95/5 molar D,L-lactide/glycolide co-polymer (1.8 g) having a weight average molecular weight of about 3600 Da and an inherent viscosity at 1% w/v in chloroform at 25° C. of 0.08 dl/g, and 95/5 molar D,L-lactide/glycolide co-polymer having a weight average molecular weight of about 15,000 Da and an inherent viscosity at 1% w/v in chloroform at 25° C. of 0.17 dl/g (4.2 g), were dissolved in anhydride-free glacial acetic acid (70 ml). The combined polymers had a weight average molecular weight of about 12,300 Da and a polydispersity of about 2.6. The goserelin-polyester solution was added dropwise to liquid nitrogen, and the frozen droplets were isolated and freeze-dried under high vacuum for about 18 hours. The product drug-polymer mixture was finally dried at 55° C. for 24 hours under high vacuum.

The dried drug-polymer mixture (6 g) was added to dichloromethane (60 ml) to give an initially cloudy colloidal mixture which, over the course of 1 hour, gradually cleared to give a clear solution of goserelin-polyester salt in dichloromethane.

This solution was spray-dried using a Buchi spray dryer, using an inlet temperature of 60° C. and an outlet temperature of 35° C., to produce approximately spherical microparticles of about 1 μm to about 10 μm diameter.

In these microparticles the drug is present essentially completely as the goserelin-polyester salt, as the acetic acid content, as free acid or anion, is 0.06% or less, instead of 0.6 to 0.7% which would be required if the goserelin were present as its acetate salt.

These microparticles when further processed by compression moulding at 80° C. yielded a clear, transparent and brittle film.

This experiment demonstrates the utility of peptide salts with benzene-soluble polyesters of low molecular weight polymers, and optionally of high polydispersity.

Similar solution, microparticle and moulded formulations may be manufactured using, in place of goserelin acetate, either naturally occurring gonadotrophin releasing hormones or other highly potent synthetic analogues (agonists or antagonists) of gonadotrophin releasing hormone, such as tryptorelin, leuprorelin, buserelin or nafarelin, preferably as the acetate salts or salts with other weak acids; or any other polypeptide hormones which controls secretion of the intact gonadotrophins or either of the gonadotrophin sub-units.

EXAMPLE 9

Goserelin acetate and other highly potent synthetic agonists of gonadotrophin releasing hormone are selective chemical castrating agents which are used in the treatment of hormone dependent cancers such as prostate cancer in men and premenopausal breast cancer in women. These drugs are also used to treat non-malignant gynaecological conditions in women, and they work by ultimately suppressing the secretions of gonadotrophins by the pituitary, which in turn leads to a suppression of the sex hormones, such as oestrogen in females and testosterone in males.

Consequently, continuous sustained release of such drugs may be evaluated in vivo in the normal adult female rat having regular oestrus cycles. In this animal, the oestrus cycle is about 4 days, and the occurrence of oestrus is shown by the presence of only cornified cells in vaginal smears, taken on the day of oestrus. If the animal is chemically castrated, by a drug such as goserelin, then oestrous does not occur, leading to the absence of cornified cells in vaginal smears. The animals will enter a prolonged period of dioestrous, induced by chemical castration, and dioestrous will be maintained for as long as effective amounts of drug are released.

(i) The microparticles obtained in Example 8 (450 mg) were dispersed in water containing 2% w/v of sodium carboxymethyl cellulose and 0.2% w/v polysorbate 80, and made up to 3 ml with water. 0.2 ml (equivalent to about 3 mg of goserelin as free base) was injected subcutaneously into 10 normal adult female rats showing regular cyclicity, and the ensuing effect on oestrous cyclicity was determined by microscopic examination of vaginal smears. The animals entered a continuous phase of dioestrous, that is chemical castration, lasting 95±3 days.

This experiment shows that an aqueous suspension formulation of goserelin-polyester salt, based on a low molecular weight benzene-soluble polyester, provides a relatively long period of controlled release of about three months of a peptide drug which has a metabolic half-life of only 4–6 hours.

(ii) The microparticles obtained in Example 8 (450 mg) were dispersed in ethyl oleate, and made up to 3 ml. Again 0.2 ml of formulation were administered to (six) female rats showing regularly cyclicity by subcutaneous injection. The animals entered a continuous phase of dioestrous lasting 81±3 days.

This experiment shows that a solution formulation of goserelin-polyester salt in an organic injection vehicle, which is a non-solvent for the polyester alone, provides a relatively long period of controlled peptide drug release.

EXAMPLE 10

Leuprorelin acetate (50.3 mg) and the co-polyester comprising 78% molar D,L-lactic acid and 22% molar glycolic acid, described in Example 6 above (453.2 mg), were dissolved in anhydride-free glacial acetic acid (5 ml). The resulting solution was added dropwise to liquid nitrogen, and the frozen droplets were freeze-dried under high vacuum for 22 hours, and then further dried at 55° C. for 24 hours under high vacuum.

The resulting product (500 mg) was dissolved in redistilled acetone (10 ml) in a 100 ml round bottomed flask, to give initially a turbid, colloidal mixture, which gradually cleared to a transparent solution. The acetone was evaporated under vacuum, and the resulting clear film was dried at 55° C. for 4 hours under high vacuum. This film of leuprorelin-polyester salt was redissolved in acetone (10 ml), and the solution was degassed and then purged with nitrogen.

Freshly distilled water (200 ml) was stirred vigorously under nitrogen, and the acetone solution of leuprorelin-polyester salt was sprayed onto the surface of the agitated water. When all the acetone solution had been sprayed, stirring was maintained for a further hour, and then the mixture was allowed to settle. The microparticles of the leuprorelin-polyester salt settled out, and the aqueous supernatant was discarded. The microparticles were resuspended in a further portion of carbon-dioxide free water (~200 ml), and the suspension was stirred under nitrogen for a further hour. The microparticles were separated, by initially allowing the mixture to settle, decanting the aqueous layer, and then filtering the residue to separate the microparticles from the excess water. The microparticles were dried at 30° C. for 24 hours under high vacuum, to give a product which had an average particle size of about 15 $\mu$m.

This microparticle formulation of leuprorelin-polyester salt was incubated in saline, buffered with phosphate to pH 7.4 at 37° C., and the supernatant was assayed periodically by UV for leuprorelin. Leuprorelin was released continuously for about 5 weeks, by which time the formulation had totally degraded.

Similar microparticle formulations may be manufactured similarly using, in place of leuprorelin, either naturally occurring gonadotrophin releasing hormones or other highly potent synthetic analogues (agonists or antagonists) of gonadotrophin releasing hormone, such as tryptorelin, goserelin, buserelin or nafarelin, preferably as the acetate salts or other salts with weak acids; or any other polypeptide hormones which controls secretion of the intact gonadotrophins or either of the gonadotrophin sub-units.

EXAMPLE 11 i) Goserelin acetate (2.28 g, equivalent to about 2.00 g of goserelin as free base) was dissolved in anhydride-free glacial acetic acid (60 ml). A mixture of two 95/5% molar poly(D,L-lactic acid)/polyglycolic acid) copolymers (12.6 g of a copolymer with a weight average molecular weight of 15,846 and a polydispersity of 1.38, and 5.4 g of a copolymer with a weight average molecular weight of 3,896 and a polydispersity of 1.78) and therefore providing an excess of copolymer carboxylic acid end groups relative to basic drug, was dissolved with stirring in anhydride-free glacial acetic acid (150 ml) to give a clear solution. The drug solution was added to the copolymer solution and was mixed thoroughly. This mixture was then added dropwise to liquid nitrogen to freeze it as small beads, and the solid material was freeze dried for two days using an Edwards high vacuum freeze drier. The dried material was further dried at 50°–55° C. in a vacuum oven for 24 hours.

This dried product (100 mg) was added to dichloromethane (1 ml) and was found to dissolve totally within 2 hours to give a clear solution. It is shown by this Example that the formation of the polyester-goserelin salt confers good solubility upon the drug such that it can be dissolved in a non-polar solvent.

ii) Goserelin acetate (2.28 g, equivalent to about 2.00 g of goserelin as free base) was dissolved in anhydride-free glacial acetic acid (60 ml). A mixture of two 100% molar poly(D,L-lactic acid) polymers (12.6 g of a polymer with a weight average molecular weight 15,178 and a polydispersity of 1.27, and 5.4 g of a polymer with a weight average molecular weight of 4,204 and a polydispersity of 1.84) and therefore providing an excess of copolymer carboxylic acid end groups relative to basic drug, was dissolved with stirring in anhydride-free glacial acetic acid (150 ml) to give a clear solution. The drug solution was added to the polymer solution and was mixed thoroughly, and this mixture was then added dropwise to liquid nitrogen to freeze it as small beads. The solid material was freeze dried for two days using an Edwards high vacuum freeze drier, and the dried material was further dried at 50°–55° C. in a vacuum oven for 24 hours.

This dried product (100 mg) was added to dichloromethane (1 ml) and was found to dissolve totally within 2 hours to give a clear solution. It is shown by this Example that the formation of the polyester-goserelin salt confers good solubility upon the drug such that it can be dissolved in a non-polar solvent.

iii) Goserelin acetate (2.28 g, equivalent to about 2.00 g of goserelin as free base) was dissolved in anhydride-free glacial acetic acid (60 ml). A mixture of an 80/20% molar poly(D,L-lactic acid)/polyglycolic acid) copolymer (12.6 g of a copolymer with a weight average molecular weight 106,510 and a polydispersity of 2.27) and a 95%/5% molar poly(D,L-lactic acid)/polyglycolic acid) copolymer (5.4 g of a copolymer with a weight average molecular weight 3,896 and a polydispersity of 1.78) and therefore providing an excess of copolymer carboxylic acid end groups relative to basic drug, was dissolved with stirring in anhydride-free glacial acetic acid (150 ml) to give a clear solution. The drug solution was added to the copolymer solution and was mixed thoroughly. This mixture was then added dropwise to liquid nitrogen to freeze it as small beads, the solid material was freeze dried for two days using an Edwards high vacuum freeze drier, and the dried material was further dried at 50°–55° C. in a vacuum oven for 24 hours.

This dried product (100 mg) was added to dichloromethane (1 ml) and was found to dissolve totally within 2 hours to give a clear solution. It is shown by this Example that the formation of the polyester-goserelin salt confers good solubility upon the drug such that it can be dissolved in a non-polar solvent.

iv) Goserelin acetate (2.17 g, equivalent to about 1.90 g of goserelin as free base) was dissolved in anhydride-free glacial acetic acid (60 ml). A mixture of two 67/33% molar poly(D,L-lactic acid)/polyglycolic acid) copolymers (12.0 g of a copolymer with a weight average molecular weight of 35,833 and a polydispersity of 1.83, and 5.15 g of a polymer with a weight average molecular weight of 4,116 and a polydispersity of 1.86) and therefore providing an excess of polymer carboxylic acid end groups relative to basic drug, was dissolved with stirring in anhydride-free glacial acetic acid (150 ml) to give a clear solution. The drug solution was added to the copolymer solution and was mixed thoroughly. This mixture was then added dropwise to liquid nitrogen to freeze it as small beads. The solid material was freeze dried for two days using an Edwards high vacuum freeze drier, and the dried material was further dried at 50°–55° C. in a vacuum oven for 24 hours.

This dried product (100 mg) was added to dichloromethane (1 ml) and was found to dissolve totally within 10 minutes to give a clear solution. It is shown by this Example that the formation of the polyester-goserelin salt confers good solubility upon the drug, such that it can be dissolved in a non-polar solvent.

COMPARATIVE EXAMPLE

Goserelin acetate (2.28 g, equivalent to about 2.00 g of goserelin as free base) was dissolved in anhydride-free glacial acetic acid (60 ml). A 50/50% molar poly(D,L-lactic acid)/polyglycolic acid) copolymer (18.0 gm polymer with a weight average molecular weight 22,307 and a polydispersity of 2.07) and therefore providing an approximately stoichiometric equivalent of copolymer carboxylic acid end groups relative to basic drug, was dissolved with stirring in anhydride-free glacial acetic acid (150 ml) to give a clear solution. The drug solution was added to the copolymer solution and was mixed thoroughly. This mixture was then added dropwise to liquid nitrogen to freeze it as small beads. The solid material was freeze dried for two days using an Edwards high vacuum freeze drier, and the dried material was further dried at 50°–55° C. in a vacuum oven for 24 hours.

This dried product (100 mg) was added to dichloromethane (1 ml) and was found not to have dissolved totally after 4 hours, but did dissolve to form a clear solution after 4 days. It is shown by this Example that the formation of the polyester-goserelin salt, to confer good solubility upon the drug such that it can be dissolved in a non-polar solvent, occurs more readily when the copolymer carboxylic acid end groups are present in excess relative to the basic drug.

The dried products i–iv were dissolved in dichloromethane and spray dried using a Buchi 190 lab scale spray drier, according to the following table:

| Product | Ratio product to solvent % | Inlet temp °C. | Outlet temp °C. |
|---|---|---|---|
| i | 10 | 48 | 32 |
| ii | 10 | 58 | 38 |
| iii | 2 | 58 | 44 |
| iv | 10 | 55 | 35 |

The spray drying of products i–iv gave small particles with a diameter approximately 1–10 μm in size as determined by scanning electron microscopy. The final particles were assayed for acetic acid content using a gas chromatography assay with a limit of detection of approximately 0.03%. No acetic acid was found in these formulations using this assay and this demonstrates that the drug is present as the polyester salt and not the acetate salt, since acetic acid levels of approximately 0.5% would be expected for the acetate salt.

Spray dried particles (50 mg) i–iv above were dissolved in dichloromethane (0.5 ml) to give a clear solution. One drop of trifluoroacetic acid was added to each, and in each case this resulted in the formation of a white precipitate. The samples were centrifuged to collect the precipitates, which were washed with dichloromethane. HPLC analysis showed the precipitated material to be goserelin. These Examples show that the drug can be displaced from the drug-polyester salt in solution in a non-polar solvent by the addition of a strong acid, and that this causes the solubility properties of the drug in non-polar solvent to return to that expected of the acid salt of a peptide drug (i.e. not soluble).

EXAMPLE 12

The spray dried particles i–iv in Example 11 were dispersed (18% w/v) in an aqueous vehicle suitable for injection (2% sodium carboxymethylcellulose [Fluka, medium viscosity], 0.2% polysorbate 80 [Tween (trade mark), Fluka].

The spray dried particles from Example 11, dispersed in the injection vehicle described above, were injected into ten female Wistar-derived rats. Blood samples were taken from the tails of five rats on days 7, 14 and 28, and these samples were assayed for goserelin using a radioimmunoassay with known specificity for the drug and proven lack of cross reactivity to metabolites.

The results of these experiments showed that this formulation achieved measurable blood levels of goserelin for at least 4 weeks.

EXAMPLE 13

Spray dried product ii of Example 11 was dispersed in the following aqueous vehicles for injection.
a. sodium carboxymethyl cellulose (medium viscosity grade, Fluka) 1.0%, and polysorbate 80 (Tween) 0.75%.
b. methyl cellulose (15 mPa.s, Fluka) 0.75% and polysorbate 80 (Tween) 0.75%.

These formulations dispersed well in these vehicles, and were suitable for parenteral administration.

EXAMPLE 14

Spray dried product ii of Example 11 (400 mg) was dissolved in dichloromethane (4 ml). This was added, using a syringe, to a solution of 0.25% polyvinyl alcohol (PVA) in water (Aldrich, 75% hydrolysed, molecular weight 2000) which was being stirred at 2500 rpm. After two minutes the rate of stirring was reduced to 800 rpm, stirring was continued for a further 30 minutes. Stirring was then stopped, and the particles formed were allowd to settle out. The PVA solution was decanted and the particles were then washed twice with ice cold water and recovered by centrifugation. The particles were finally dried by freeze drying, and the final product was a fine particulate material containing goserelin.

EXAMPLE 15

Spray dried formulation iv of Example 11 was extruded at 82° C. to give a cylindrical extrudate approximately one millimeter in diameter. This extrudate was cut to lengths weighing approximately 36 mg and containing approximately 3.6 mg of goserelin. This extrudate was completely clear to light rather than being of a white appearance, the latter appearance being typical of a simple mixture of drug and polymer produced without forming the salt of the peptide with the polyester (as in for example the commercially available 'Zoladex' depot—'Zoladex' is a trade mark). The clarity of this extrudate indicates that the peptide goserelin is compatible with the polyester phase, rather than being in a separate phase, which results in light scattering and a white appearance. This compatibility can only occur if the peptide is in the same phase as the polymer, i.e. it is present as the salt of the polyester.

Single such 3.6 mg depots were implanted into 21 Wistar-derived rats under anaesthesia. At subsequent time points groups of three animals were killed and the depots were retrieved. The recovered depots were dissolved in glacial acetic acid in a volumetric flask and the polymer was precipitated by addition of an excess of water. This was then filtered (Millex 0.5 $\mu$m) and the filtrate assayed for drug content by HPLC. The release profile of the depots was calculated by reference to the drug content of depots which had not been implanted, and which were included in the same assay. These depots of drug-polyester salt gave sustained release of goserelin in vivo for a period of at least four weeks.

EXAMPLE 16

(i) Lactide/glycolide copolymer (95/5) with a single terminal carboxylic acid group (8.87 g, Mw=5750, polydispersity=1.5, molecular weight by end group titration=2516 g/mole, inherent vicosity at 1% w/v in chloroform=0.10 dl/g) was dissolved in dichloromethane (50 ml) with stirring. To this was added 1.13 g goserelin acetate, forming a cloudy suspension. Methanol (5 ml) was added with stirring, and after 30 minutes the mixture was completely clear. The solvent was then removed from the solution by rotary evaporation to leave a clear solid. This solid was redissolved in dichloromethane (50 ml) and the solvent was again removed by rotary evaporation. The redissolution step and solvent removal step were repeated twice more to leave a very viscous fluid which was dried under high vacuum to give a white foam. The foam was broken up and dried under vacuum for a further 24 hours at room temperature to give a fine amorphous solid.

(ii) The process described in i) above was repeated, using a lactide/glycolide copolymer (75/25) with a single terminal carboxylic acid (8.87 g, Mw=10900, polydispersity=1.85, molecular weight by end group titration=3210 g/mole, inherent viscosity at 1% w/v in chloroform =0.14 dl/g), to give a fine amorphous solid.

Formulation 1

The goserelin-lactide/glycolide polymer salt from (i) above (1 g) was added to benzyl benzoate (99%, ex Janssen, 2 ml) and this was heated using a hand held hot-air gun whilst agitating the mixture until the solid was dissolved. 110 $\mu$l of this solution formulation contained 3.6 mg of goserelin.

Formulation 2

As Formulation 1, except that the solvent was a mixture (1.7 ml) of 67% benzyl benzoate (99%, ex Janssen) and 33% benzyl alcohol (anhydrous, 99%, ex Aldrich). 100 $\mu$l of this solution formulation contained 3.6 mg of goserelin.

Formulation 3

As Formulation 1, except that the solvent was benzyl alcohol (1.7 ml, anhydrous, 99%, ex Aldrich). 100 $\mu$l of this solution formulation contained 3.6 mg of goserelin.

Formulation 4

As Formulation 1, except that the goserelin-lactide/glycolide polymer salt from (ii) above (1 g) and 3 ml of benzyl benzoate were used. 150 $\mu$l of this solution formulation contained 3.6 mg of goserelin.

Formulation 5

As Formulation 4, except that the solvent mixture of Formulation 2 was used. 100 $\mu$l of this solution formulation contained 3.6 mg of goserelin.

Formulation 6

As Formulation 4, except that the solvent of Formulation 3 was used. 100 $\mu$l of this solution formulation contained 3.6 mg of goserelin.

Biological Evaluation

Release of goserelin from the above Formulations 1 to 6 in vivo was determined by studying daily vaginal smears of dosed female rats. The normal oestrus cycle (oestrus, dioestrus, met-oestrus, pro-oestrus), can be followed from the proportions of the various cell types (leucocytic, epithelial and cornified) in the smear. If the release of drug from the formulations is continuous the normal oestrus cycle is interrupted and the rats will remain in dioestrus as long as release of the goserelin continues.

Formulations 1–6 were dosed to groups (n=6) of regularly cycling female rats at a dose of 3.6 mg goserelin per rat. A syringe fitted with a 20 gauge needle was used for dosing the formulations subcutaneously. An undosed group of five rats was used as a control group. Vaginal smears were taken daily from the rats, and examined to determine the oestrus state of the animals, and the results obtained were as follows:

| Formulation number | Average duration of dioestrus (days) (± s.e.) |
| --- | --- |
| 1 | 100 ± 2.7 |
| 2 | 120 ± 6.3 |
| 3 | 69 ± 5.9 |
| 4 | 59 ± 1.2 |
| 5 | 61 ± 2.1 |
| 6 | 53 ± 3.7 |

From these results it can be seen that all six formulations gave periods of goserelin release in excess of 6 weeks and that formulations 1 and 2 released goserelin for a period of three months or more. It can further be seen from these examples that the formulations of the goserelin-polyester salt can be provided as solutions which can be readily administered parentally using a narrow gauge needle, and that such formulations are convenient for treatment of hormone dependent tumours in man.

EXAMPLE 17

Formulation 1

As Formulation 1 from Example 16.

Formulation 2

The process described in Example 16(i) was repeated, using a polylactide homopolymer with a single terminal carboxylic acid (Mw=5092, polydispersity=1.44, molecular weight by end group titration=2270 g/mole) and goserelin acetate (0.46 g). The acetic acid content of this amorphous solid was determined by gas chromatography and was found to be 0.14%.

This goserelin-lactide polymer salt (1 g) was added to benzyl benzoate (99%, ex Janssen, 2 ml), and this was heated using a hand held hot-air gun whilst agitating the mixture until the solid was dissolved. 110 $\mu$l of this solution formulation contained 3.6 mg of goserelin.

Formulation 3

A lactide/glycolide copolymer (95/5) with a single terminal carboxylic acid (7.86 g, MW=5750, polydispersity=1.50, molecular weight by end group titration=2516 g/mole) and goserelin acetate (0.98 g) were dissolved in glacial acetic acid (100 ml). This solution was frozen by adding dropwise to liquid nitrogen, followed by freeze drying for 2 days. The resulting solid was then dried for a further 24 hours at 40° C. The acetic acid content of this freeze dried solid was determined by gas chromatography and was found to be 0.17%.

This goserelin-lactide/glycolide copolymer mixture (1 g) was added to benzyl benzoate ((2 ml, 99%, ex Janssen), and this was heated using a hand held hot-air gun whilst agitating the mixture until the solid was dissolved. 110 $\mu$l of this solution formulation contained 3.6 mg of goserelin.

It can therefore be seen that formulation of goserelin as the polyester salt confers good solubility properties upon the drug, such that it can be dissolved in lipophilic solvents such as benzyl benzoate in which goserelin acetate itself is not soluble.

Biological Evaluation

Formulations 1–3 were dosed to groups (n=10) of regularly cycling female rats at a dose of 3.6 mg goserelin per rat, as described in Example 16. Following dosing, the animals were found to enter a period of continuous dioestrus indicating continuous release of goserelin. The average duration of the diostrus period for each group of rats is given in the following table. From this table it can be seen that all three formulations gave periods of goserelin release in excess of fourteen weeks.

| Formulation No. | Average duration of dioestrus (days) (± s.e.) |
| --- | --- |
| 1 | 104 (± 5.4) |
| 2 | 99 (± 3.9) |
| 3 | 101 (± 2.8) |

It can further be seen from these examples that the formulations of the goserelin polyester salt can be provided as solutions which can be readily administered parentally using a narrow gauge needle, and that such formulations are convenient for the treatment of hormone dependent tumours in man.

EXAMPLE 18

Formulation 1

Lactide/glycolide copolymer (95/5) with a single terminal carboxylic acid (4.5 g, Mw=6806, polydispersity=1.55, molecular weight by end group titration=3027 g/mole, inherent vicosity at 1% w/v in chloroform=0.108 dl/g) was dissolved in glacial acetic acid (50 ml). To this solution was added goserelin acetate (0.56 g, equivalent to 0.5 g goserelin) and the mixture was stirred for 10 minutes to give a clear colourless solution. This was frozen by adding dropwise to liquid nitrogen, followed by freeze drying for 2 days. The resulting solid was then dried for a further 24 hours at 40° C. The acetic acid content of this freeze dried solid was determined by gas chromatography and was found to be 0.3%.

This goserelin-lactide/glycolide copolymer mixture (1.0 g) was added to benzyl benzoate (2.0 ml, 99%, ex Janssen) and was dissolved with warming and agitation. The final solution contained 3.67 mg of goserelin in 110 $\mu$l, and the goserelin content of the final product was 10.0% w/w.

Formulation 2

The process described above for Formulation 1 was repeated, using a lactide/glycolide copolymer (95/5) with a single terminal carboxylic acid (4.0 g, Mw=6011, polydispersity=1.56, molecular weight by end group titration=2700 g/mole, inherent vicosity at 1% w/v in chloroform=0.099 dl/g and 1.12 g of goserelin acetate (equivalent to 1.0 g of goserelin). The acetic acid content of this freeze dried solid was determined by gas chromatography and was found to be 0.83% and the goserelin content of the final product was 19.46% w/w.

This goserelin-lactide/glycolide copolymer mixture (0.54 g) was added to benzyl benzoate (2.46 ml, 99%, ex Janssen) and was dissolved with warming and agitation. The final solution contained 3.50 mg of goserelin in 110 $\mu$l.

Formulation 3

The process described above for Formulation 2 was repeated, using 2.1 g of the lactide/glycolide copolymer and 1.0 g of goserelin acetate (equivalent to 0.9 g of goserelin). The acetic acid content of this freeze dried solid was determined by gas chromatography and was found to be 1.14%, and the goserelin content of the final product was 28.91% w/w.

This goserelin-lactide/glycolide copolymer mixture (0.36 g) was added to benzyl benzoate (2.64 ml, 99%, ex Janssen) and was dissolved with warming and agitation. The final solution contained 3.47 mg of goserelin in 110 μl.

Formulation 4

The process described above for Formulation 1 was repeated, using a lactide/glycolide copolymer (95/5) with a single terminal carboxylic acid (8.66 g, Mw=5604, polydispersity=1.71, molecular weight by end group titration =1960 g/mole, inherent vicosity at 1% w/v in chloroform=0.094 dl/g and 1.08 g of goserelin acetate (equivalent to 0.96 g of goserelin). The acetic acid content of this freeze dried solid was determined by gas chromatography and was found to be 0.08% and the goserelin content of the final product was 9.90% w/w.

This goserelin-lactide/glycolide copolymer mixture (1.0 g) was added to benzyl benzoate (2.0 ml, 99%, ex Janssen) and was dissolved with warming and agitation. The final solution contained 3.67 mg of goserelin in 110 μl.

Biological Evaluation

Formulations 1–4 were dosed to groups (n=9 or 10) of regularly cycling female rats at a dose of 3.6 mg goserelin per rat, as described in Example 16. Following dosing, the animals were found to enter a period of continuous dioestrus indicating continuous release of goserelin. The average duration of the diostrus period for each group of rats is given in the following table. From this table it can be seen that all three formulations gave periods of goserelin release for a period of about 3 months or more.

| Formulation No. | Average duration of dioestrus (days) (± s.e.) |
|---|---|
| 1 | 114 ± 1.8 |
| 2 | 94 ± 4.6 |
| 3 | 97 ± 5.3 |
| 4 | 83 ± 4.3 |

It can further be seen from these examples that the formulations of the drug polyester salt can be provided as solutions which can be readily administered parentally using a narrow gauge needle, and that such formulations are convenient for treatment of hormone dependent tumours in man.

EXAMPLE 19

The goserelin-polyester salt (ii) of Example 16 (3.75 g) was dissolved in dichloromethane (50 ml) which had previously been filtered through a 0.45 μm filter. This solution was filtered through a 0.5 μm teflon filter membrane (Whatman WTP) into a flask which had been sterilised using an autoclave. The solvent was removed using a rotary evaporator to give a viscous liquid, and air was then admitted to the rotary evaporator through a 0.5 μm filter. The viscous liquid was warmed and dried under vacuum to give a white foam. The foam obtained was weighed into autoclaved crimp-top vials in a laminar flow cabinet and freshly distilled solvents were added to give solution formulations of the goserelin-polyester salt which were essentially particulate-free.

Formulation 1

1 g of the solid was added to benzyl benzoate (distilled, bp 106° C. at 0.3 mb, 3 ml) and was warmed using a hot-air gun until dissolved. 145 μl of this solution formulation contained 3.6 mg of goserelin.

Formulation 2

1 g of the solid was added to benzyl alcohol (distilled, bp 44° C. at 0.3 mb, 1.7 ml) and was warmed using a hot-air gun until dissolved. 100 μl of this solution formulation contained 3.6 mg of goserelin.

Biological Evaluation

Two groups of ten female rats were dosed subcutaneously using a 20 gauge needle with formulations 1 and 2 at a dose of 3.6 mg per rat. Terminal blood samples were taken from the rats at subsequent timepoints (1 week (n=4), 4 weeks and 6 weeks (n=3)). The blood samples were assayed for goserelin by means of radioimmunoassay. Measurable blood levels of goserelin were found with both formulations, indicating that the solution formulations gave sustained drug release for several weeks. The blood level profile of formulation 1 was found to peak at about four weeks, whereas with formulation 2 the peak occurred at week one and thereafter the blood levels were found to decline progressively with time. The blood level profile of formulation 1 is considered to be more desirable than that of formulation 2 due to the more constant blood levels obtained when benzyl benzoate is used as the solvent for the solution formulation.

It can further be seen from these examples that the formulations of the drug polyester salt can be provided as solutions which can be readily administered parentally using a narrow gauge needle, and that such formulations are convenient for treatment of hormone dependent tumours in man.

EXAMPLE 20

A lactide/glycolide copolymer (95/5) with a single terminal carboxylic acid (9.0 g, Mw=6011, polydispersity=1.56, molecular weight by end group titration=2700 g/mole, inherent vicosity at 1% w/v in chloroform=0.099 dl/g) was dissolved in dichloromethane (100 ml). To this was added goserelin acetate (1.124 g, equivalent to 1 g of goserelin) with stirring, followed by the addition of methanol (10 ml). The cloudy suspension obtained was stirred at room temperature for about one hour until a clear solution was obtained. The solvent was removed using a rotary evaporator to give a clear viscous liquid. This was then redissolved in dichloromethane and redried as before. This step was repeated twice more, and the viscous liquid finally obtained was dried under high vacuum to produce a white foam, which was further vacuum dried overnight. The foam was broken to a fine powder which was vacuum dried for one day at room temperature. To this powder was added benzyl benzoate (20 ml, 99%, ex Janssen) and the resultant mixture was gently warmed, with agitation, to obtain a solution.

Biological Evaluation

This solution formulation of goserelin was dosed subcutaneously using a 20 gauge needle into each of 45 female rats (220 μl, equivalent to 7.3 mg goserelin). Groups of five rats were terminated and blood samples taken at 1 and 4 days, and 1, 3, 5, 7, 9, 11 and 13 weeks. In addition blood samples were taken from the tail vein of groups of five rats at 2, 4, 6, 8, 10 and 12 weeks. The samples were analysed for goserelin by means of radioimmunassay, and the results show that this liquid formulation of goserelin-polyester salt gave measurable blood levels of drug for about 11 weeks after dosing and shows that the formulation gives sustained release of goserelin in vivo.

It can further be seen from these examples that the formulations of the drug polyester salt can be provided as solutions which can be readily administered parentally using a narrow gauge needle, and that such formulations would be convenient for treatment of hormone dependent tumours in man.

EXAMPLE 21

The peptide known as Substance P, in the form of its acetate salt (ex Sigma, 2 mg) was added to dichloromethane (3 ml) and thoroughly agitated. The peptide showed no indication of dissolving in the solvent, and remained as a cloudy suspension.

A lactide/glycolide copolymer (70/30) with a single terminal carboxylic acid (225 mg, Mw=9755, polydispersity= 1.52, molecular weight by end group titration=1800), was added to dichloromethane (25 ml). This was stirred for 15 minutes to give a clear colourless solution. To this was added a solution of Substance P (25 mg) in methanol (0.5 ml). The resulting cloudy suspension was stirred for 1 hour, by which time a completely clear solution had formed. The solvent was removed by rotary evaporation and the clear 'glassy' solid obtained was redissolved in dichloromethane (5 ml) and reevaporated. This was repeated twice. The final solid was dissolved in dichloromethane (3 ml) and the solution was dropped slowly onto PTFE coated cloth, allowing the solvent to evaporate to form a thin film of a clear colourless glassy solid (peptide content 9.1% w/w).

This film (96.8 mg) was placed in a small vial and phosphate buffered saline (2 ml, pH 7.4) was added (buffer was previously filtered through a 0.2 $\mu$m filter and contained 0.02% sodium azide as a preservative). The vial was placed in an incubator at 37° C. and the buffer was removed and replaced periodically. The buffer which was removed was analysed for release of Substance P, using an ultraviolet spectrophotometer (Hewlett Packard 8452A) at 210 nm, against standard solutions of substance P. The results show that Substance P can be dissolved in dichloromethane when formed as the salt of a carboxy-terminated lactide/glycolide copolymer, and can be processed in this solvent to give a thin film, which gives continuous release of the peptide for a period of about 4 weeks.

EXAMPLE 22

An aqueous solution of leuprolide acetate (otherwise known as leuprorelin acetate), (300 $\mu$l of a 330 mg/ml solution) is added under high shear conditions, to 20 ml of a 10% w/w solution of poly(hydroxystearic acid) having a number average molecular weight of about 2000, in Higlyol 812 (triglycerides of medium chain saturated fatty acids including linolenic acid, ex Dynamit Nobel, UK), to form the leuprolide-polymer salt, in part, at the oil/aqueous interface, which salt stabilises the resultant water-in-oil colloidal suspension. The water is removed at 50° C. by stirring under high vacuum until the mixture no longer froths and bubbles, to give an oily composition which exhibits a very faint haze, and which is suitable for oral administration.

EXAMPLE 23

Lys$^8$-vasopressin acetate salt (2 mg, ex Sigma) was added to dichloromethane (3 ml) and agitated. The peptide showed no indication of dissolving in the solvent and remained as a cloudy suspension.

A lactide/glycolide copolymer (70/30) with a single terminal carboxylic acid (225 mg, Mw=9755, polydispersity= 1.52, molecular weight by end group titration=1800), was added to dichloromethane (5 ml). This mixture was stirred for 15 minutes to give a clear colourless solution. To this was added Lys$^8$-vasopressin (25 mg, ex Sigma) and methanol (0.5 ml). The resulting cloudy suspension was stirred for 1 hour, by which time a completely clear solution had formed. The solvent was removed by rotary evaporator and the clear 'glassy' solid obtained was redissolved in dichloromethane (5 ml) and re-evaporated. This was repeated twice. The final solid was dissolved in dichloromethane (3 ml) and the solution was dropped slowly onto PTFE coated cloth, allowing the solvent to evaporate to form a thin film of a clear colourless glassy solid (Lys$^8$-vasopressin content 10% w/w).

This film (97.31 mg) was placed in a small vial and phosphate buffered saline (2 ml, pH 7.4) was added (buffer was previously filtered through a 0.2 $\mu$m filter and contained 0.02% sodium azide as a preservative). The vial was placed in an incubator at 37° C. and the buffer was removed and replaced periodically. The buffer was analysed for release of Lys$^8$-vasopressin using an ultraviolet spectrophotometer (Hewlett Packard 8452A) at 210 nm against standard solutions of Lys$^8$-vasopressin. The results of this test are shown in the following table. The experiment shows that Lys$^8$-vasopressin can be dissolved in dichloromethane, when formed as the salt of a carboxy-terminated lactide/glycolide copolymer, and that the resulting mixture gives continuous release of the peptide for a period of at least four weeks. Release of Lys$^8$-vasopressin in vitro

| Time (days) | Release of Lys$^8$-vasopressin from film (%) |
|---|---|
| 1 | 4.11 |
| 4 | 5.45 |
| 7 | 5.55 |
| 14 | 5.75 |
| 21 | 26.82 |
| 28 | 47.27 |

EXAMPLE 24

Two formulations of ZENECA ZD6003 ([Met$^{-1}$, Arg$^{11}$, Ser$^{17,27,60,65}$] human G-CSF (granulocyte-colony stimulating factor) modified with polythylene glycol 5000 as described in Reference Example 4 or 7 of European Patent Publication No. 0 473 268) in lactide/glycolide copolymer were prepared as follows.

(i) Dichloromethane (4 ml) was added to a freeze-dried preparation of ZD6003 (39.72 mg). This resulted in an opaque dispersion of drug in the solvent. A lactide/ glycolide copolymer (75/25) with a single terminal carboxylic acid (363.6 mg, Mw=9963, polydispersity=2.19, molecular weight by end group titration=2815) was added, and a clear solution formed.

This solution was added to a solution (400 ml) of methyl cellulose (0.25% w/v Methocel, 15 mPa.s, ex Fluka) in water under shear (2150 RPM, Heidolph RZR50 stirrer). After stirring at this rate for 3 minutes the stirring speed was reduced to 800 RPM. The resulting particles were then allowed to settle under gravity for 30 minutes, whilst keeping the solution cool over ice. The supernatant was then discarded and the particles were washed by resuspending in ice-cold distilled water (50 ml), and centrifugation at 1000

RPM. This was repeated four times and the particles were then finally freeze dried.

Particles made in this way were of good quality, being spherical and of a mean size of 32 μm as determined by image analysis from optical microscopy. The drug content of these particles was determined by extraction followed by HPLC analysis and was found to be 9.45%, representing an incorporation efficiency of 96% of the drug used to form the microparticles.

(ii) Dichloromethane (4 ml) was added to a freeze-dried preparation of ZD6003 (44.18 mg). This resulted in an opaque dispersion of drug in solvent. A lactide/glycolide copolymer (75/25, 364.1 mg, Mw=16,800 by size exclusion chromatography, polydispersity=2.2, ex Boehringer Ingelheim) was added. An attempt to determine the molecular weight of the polymer by end group titration was performed, but was not possible due to very low levels of titratable moieties, and consequently this polymer does not have a terminal carboxylic acid. The mixture of the drug solution and the polymer did not become clear upon addition of the polymer and the mixture remained as a turbid dispersion, indicating that, as expected, in the absence of acid end groups in the polymer, no peptide-polyester salt could form.

This mixture was added to a solution (400 ml) of methyl cellulose (0.25% w/v Methocel, 15 mPa.s, Fluka) in water under shear (2150 RPM, Heidolph RZR50 stirrer). After stirring at this rate for three minutes the stirring speed was reduced to 800 RPM. The resulting particles were then allowed to settle under gravity for 30 minutes, whilst keeping the solution cool over ice. The supernatant was then discarded and the particles were washed by resuspending in distilled water (50 ml) and centrifugation at 1000 RPM. This was repeated four times and the particles were then finally freeze dried.

Particles made in this way were of inferior quality, compared with those obtained in (i) above, with some being of irregular shape and of a mean size of 40 μm as determined by image analysis from optical microscopy. The drug content of these particles was determined by extraction followed by HPLC analysis and was found to be 2.05%, representing an incorporation efficiency of 19% of the drug used to form the microparticles.

The above example shows that ZD6003 can be dissolved in dichloromethane when in the presence of a polymer with a single terminal carboxylic acid, despite dichloromethane iself being a non-solvent for the drug. In addition such a solution can be used to form microparticles of drug and polymer with a very high rate of incorporation of drug. In contrast, the above example also shows that ZD6003 cannot be dissolved in dichloromethane in the presence of a polymer, when such a polymer does not have a terminal carboxylic acid, and forms only a hazy dispersion. Furthermore such hazy dispersions of ZD6003 in a solution of polymer with no terminal carboxylic acid result in poor incorporation of drug when processed to form microparticles.

EXAMPLE 25

(i) Goserelin acetate (22.47 mg, equivalent to 19.99 mg goserelin) was added to benzyl benzoate (2.21 g, 99%, ex Janssen). This mixture was placed in an incubator at 40° C. and was stirred continuously for 9 days using a magnetic stirrer. After 2 and 9 days aliquots were taken and centrifuged for 15 minutes at 13,000 RPM to pellet undissolved drug. Aliquots of supernatant (approx. 100 mg) were weighed accurately into 50 ml volumetric flasks. To each was added glacial acetic acid (2 ml), followed by making up to volume with an aqueous solution of trifluoroacetic acid (0.5% v/v). A portion of this solution was placed in a centrifuge tube and was centrifuged at 13,000 RPM for 15 minutes to separate suspended material. The supernatant was then assayed for goserelin content, using HPLC. No goserelin was detectable in either sample. The limit of detection of goserelin in this HPLC assay was 0.2 μg/ml and the limit of quantification was 0.5 μg/ml. Thus the equilibrium solubility (at 40° C.) of goserelin in benzyl benzoate can be estimated from the above as less than 0.2 mg/ml.

(ii) A lactide/glycolide copolymer (95/5) with a single terminal carboxylic acid (291.9 mg, Mw=6742, polydispersity=1.61, molecular weight by end group titration=2565 gm/mole, inherent vicosity at 1% w/v in chloroform=0.103 dl/g) was added to benzyl benzoate (3.38 g, 99%, ex Janssen) to form a solution. To this was added goserelin acetate (22.52 mg, equivalent to 20.03 mg goserelin). This mixture was incubated and sampled as described in (i) above. No goserelin was detectable in the benzyl benzoate at 2 days, but at 9 days a level of approximately 0.2 μg goserelin per ml of benzyl benzoate was detected. The limit of detection of goserelin in this HPLC assay was as indicated in (1) above. From this it can be shown that the equilibrium solubility (at 40° C.) of goserelin in benzyl benzoate, when present as a simple mixture with a lactide/glycolide copolymer, can be estimated as 0.2–0.5mg/ml.

(iii) A lactide/glycolide copolymer (95/5) with a single terminal carboxylic acid (9.0 g, Mw=6011, polydispersity=1.56, molecular weight by end group titration=2700 g/mole, inherent vicosity at 1% w/v in chloroform=0.099 dl/g) was dissolved in dichloromethane (100 ml). To this was added goserelin acetate (1.124 g, equivalent to 1 g goserelin) with stirring, followed by the addition of methanol (10 ml). The cloudy suspension obtained was stirred at room temperature for about 1 hour until a clear solution was obtained. The solvent was removed using a rotary evaporator to give a clear viscous liquid. This was then redissolved in dichloromethane and redried as before. This step was then repeated twice more and the viscous liquid finally obtained was dried under high vacuum to produce a white foam, which was further vacuum dried overnight. The foam was broken to a fine powder which was vacuum dried for 1 day at room temperature. To this powder was added benzyl benzoate (20 ml, 99%, ex Janssen) and the resultant mixture was gently warmed, with agitation, to obtain a solution.

The solution was thoroughly mixed and a 1ml sample was placed in a centrifuge and spun at 14,000 RPM for 30 minutes. An aliquot of the supernatant was carefully removed and weighed into a 50 ml volumetric flask. The sample was assayed for goserelin content as described in (i). The goserelin content of this solution was found to be 24.6 mg/ml benzyl benzoate.

This example shows that benzyl benzoate is a very poor solvent for goserelin acetate. Furthermore, the addition of a lactide/glycolide polymer to form a simple mixture with goserelin acetate in benzyl benzoate does not lead to a marked increase in the equilibrium solubility of goserelin acetate in benzyl benzoate. However, goserelin/polyester salt could be dissolved in benzyl benzoate to form a solution containing goserelin at a concentration very much higher than the estimated equilibrium solubility of free goserelin in this solvent.

I claim:

1. A composition suitable for injection, comprising a salt formed from a cation derived from a peptide containing one or more basic groups and an anion derived from a carboxy-terminated polyester, wherein said salt is dissolved in a pharmaceutically acceptable organic solvent which is a solvent for the free polyester but not a solvent for the free peptide, and wherein the peptide present in said composition is essentially completely in the form of said peptide/polyester salt.

2. A composition as claimed in claim 1 wherein the peptide is pharmacologically active, and is selected from the group consisting of oxytocin, vasopressin, adrenocorticotrophic hormone (ACTH), epidermal growth factor (EGF), prolactin, luteinising hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumour necrosis factor, colony stimulating factors, motilin, bombesin, dinorphin, neurotensin, cerulein, bradykinin, urokinase, kallikrein, substance P analogues and antagonists, angiotensin II, nerve growth factor, blood coagulation factor VII and IX, renin, bradykinin, tyrocidin, gramicidines, growth hormones, melanocyte stimulating hormone, thyroid hormone releasing hormone, thyroid stimulating hormone, parathyroid hormone, pancreozymin, cholecystokinin, human placental lactogen, human chorionic gonadotrophin, protein synthesis stimulating peptide, gastric inhibitory peptide, vasoactive intestinal peptide, platelet derived growth factor, growth hormone releasing factor, and bone morphogenic protein, and synthetic analogues and pharmacologically-active fragments thereof.

3. A composition as claimed in claim 1 wherein the peptide is pharmacologically inactive and is selected from the group consisting of polyarginine, polylysine and poly (arginine-co-lysine), (co-)polymers of neutral amino acids, in D-, L- or DL-form, with arginine, lysine or arginine and lysine in D-, L- or racemic form, or peptides or (co-)polypeptides in which the peptide chains are terminated in whole or in part by a basic group at the N-terminus and the backbone is comprised of neutral amino acid residues.

4. A composition as claimed in claim 2 wherein the basic peptide drug is a synthetic analogue of luteinising hormone releasing hormone, selected from the group consisting of buserelin ([D-Ser(Bu$^t$)$^6$, des-Gly-NH$_2$$^{10}$]-LHRH(1–9) NHEt), deslorelin ([D-Trp$^6$, des-Gly-NH$_2$$^{10}$]-LHRH(1–9) NHEt), fertirelin ([des-Gly-NH$_2$$^{10}$]-LHRH(1–9)NHEt), goserelin ([D-Ser(Bu$^t$)$^6$, Azgly$^{10}$]-LHRH), histrelin ([D-His (Bzl)$^6$, des-Gly-NH$_2$$^{10}$]-LHRH(1–9)NHEt), leuprorelin ([D-Leu$^6$, des-Gly-NH$_2$$^{10}$]-LHRH(1–9)NHEt), lutrelin ([D-Trp$^6$, MeLeu$^7$, des-Gly-NH$_2$$^{10}$]-LHRH(1–9)NHEt), nafarelin ([D-Nal$^6$]-LHRH), and tryptorelin ([D-Trp$^6$]-LHRH), and pharmacologically active salts thereof.

5. A composition as claimed in claim 1 wherein the pharmaceutically acceptable solvent is selected from the group consisting of benzyl benzoate, benzyl alcohol, ethyl lactate, glyceryl triacetate, esters of citric acid, and low molecular weight (<1000) polyethylene glycols, alkoxy-polyethylene glycols and polyethylene glycol acetates.

6. The composition as claimed in claim 1 wherein the polyester is selected from the group consisting of polyesters derived from hydroxy-acids, polyesters derived from the polycondensation of diols with dicarboxylic acids, polyesters derived from the polycondensation of polyols with polycarboxylic acids, and polyesters derived from ring opening polycondensation of acid dimers.

7. The composition as claimed in claim 1, wherein the carboxylic acid end groups of said polyester are present in a stoichiometric excess relative to the basic groups of said peptide.

8. Microparticles suitable for injection comprising a composition consisting essentially of a salt formed from a cation derived from a peptide containing one or more basic groups and an anion derived from a carboxy-terminated polyester, wherein the peptide present in said composition is essentially completely in the form of peptide/polyester salt.

9. Microparticles suitable for injection comprising a composition consisting essentially of a salt formed from a cation derived from a peptide containing one or more basic groups and an anion derived from a carboxy-terminated polyester, said composition being characterized by being soluble in a non-solvent for said peptide, as determined by forming a clear solution in dichloromethane.

10. The microparticles as claimed in claim 8 or 9, wherein the carboxylic acid end groups of said polyester are present in a stoichiometric excess relative to the basic groups of said peptide.

11. An injectable composition comprising microparticles as claimed in claim 8 or 9 having a diameter of 0.2 $\mu$m to 500 $\mu$m suspended in a pharmaceutically acceptable injection vehicle, wherein said microparticles comprise a composition consisting essentially of a salt of a pharmaceutically active peptide with said polyester.

12. The injectable composition of claim 11 wherein said microparticles are suspended in an aqueous injection vehicle.

13. The injectable composition of claim 11 wherein said microparticles are suspended in an organic injection vehicle.

14. The injectable composition of claim 11 wherein the polyester comprises a homo- or co-polymer of lactic acid and glycolic acid.

15. The injectable composition of claim 13 wherein the injection vehicle is selected from the group consisting of ethyl oleate, isopropyl myristate, vegetable oil, fatty glycerides and mixtures thereof.

16. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of said polyester carboxylic acid end groups relative to said basic peptide groups, obtainable by a process comprising i) dissolving the basic peptide and carboxy-terminated polyester in a first solvent in which both the peptide and the polyester are soluble to form a first solution;

ii) freezing said first solution at high speed to form a frozen mixture;

iii) freeze-drying the frozen mixture to remove said first solvent, forming a freeze-dried product;

iv) dispersing the freeze-dried product into a second solvent which is a solvent for the polyester and a non-solvent for the peptide to form a second solution containing said peptide/polyester salt; and v) removing said second solvent from said second solution by a procedure selected from the group consisting of spray-drying, spray-congealing, evaporation and phase separation coacervation to form a solid product which is in the form of microparticles, or from which said microparticles are thereafter formed.

17. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of said polyester carboxylic acid end groups relative to said basic peptide groups, obtainable by a process comprising
   i) dissolving the basic peptide and carboxy-terminated polyester in a first solvent in which both the peptide and the polyester are soluble to form a first solution;
   ii) freezing said first solution at high speed to form a frozen mixture;
   iii) freeze-drying the frozen mixture to remove said first solvent, forming a freeze-dried product;
   iv) dispersing the freeze-dried product into a second solvent which is a solvent for the polyester and a non-solvent for the peptide to form a second solution containing said peptide/polyester salt;
   v) dispersing said second solution in an aqueous phase to form an aqueous dispersion; and
   vi) drying said aqueous dispersion to form a solid product which is in the form of microparticles, or from which said microparticles are thereafter formed.

18. The microparticles according to claim 17 wherein the aqueous dispersion is dried by a method selected from the group consisting of removal of said second solvent in vacuo followed by freeze drying; and removal of said second solvent and water in a single freeze drying step.

19. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of said polyester carboxylic acid end groups relative to said basic peptide groups, obtainable by a process comprising
   i) dissolving the basic peptide and carboxy-terminated polyester in a first solvent in which both the peptide and the polyester are soluble to form a first solution;
   ii) freezing the first solution at high speed to form a frozen mixture;
   iii) freeze-drying the frozen mixture to remove said first solvent, forming a freeze-dried product;
   iv) dispersing the freeze-dried product into a second solvent which is a solvent for the polyester and a non-solvent for the peptide to form a second solution containing said peptide/polyester salt;
   v) dispersing the second solution in an aqueous phase to form an aqueous dispersion containing microparticles;
   vi) separating said microparticles from said aqueous dispersion; and
   vii) drying said microparticles.

20. The microparticles according to claim 17 or 19, wherein the aqueous phase comprises a viscosity-enhancing polymer.

21. The microparticles according to claim 17 or 19, wherein step v) is carried out in the absence of carbon dioxide in an inert atmosphere.

22. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of said polyester carboxylic acid end groups relative to said basic peptide groups, obtainable by a process comprising
   i) dissolving the basic peptide and carboxy-terminated polyester in a first solvent in which both the peptide and the polyester are soluble to form a first solution;
   ii) freezing said first solution at high speed to form a frozen mixture;
   iii) freeze-drying the frozen mixture to remove said first solvent, forming a freeze-dried product;
   iv) dispersing the freeze-dried product into a second solvent which is a solvent for the polyester and a non-solvent for the peptide to form a second solution containing said peptide/polyester salt;
   v) removing said second solvent from the second solution to form a first solid product;
   vi) subjecting the first solid product to polymer melt processing techniques to form a second solid product; and
   vii) reducing the size of the second solid product to form said microparticles.

23. The microparticles according to claim 22 wherein step vii) is carried out by a procedure selected from the group consisting of comminution and milling.

24. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of polyester carboxylic acid end groups relative to basic peptide group, obtainable by a process comprising
   i) dissolving the carboxy-terminated polyester in a first solvent to form a first solution;
   ii) dissolving the basic peptide in a hydroxylic solvent to form a second solution;
   iii) adding said second solution to said first solution to form a third solution; and
   iv) removing the first solvent and hydroxylic solvent from the third solution to form a solid product which is in the form of microparticles, or from which said microparticles are thereafter formed.

25. The microparticles according to claim 24 wherein step iv) is carried out by a procedure selected from the group consisting of spray-drying, evaporation, freeze drying, phase separation coacervation, and spray-congealing.

26. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of polyester carboxylic acid end groups relative to basic peptide groups, obtainable by a process comprising
   i) dissolving the carboxy-terminated polyester in a first solvent to form a first solution;
   ii) adding the basic peptide to said first solution to form a mixture;
   iii) adding a hydroxylic solvent to the mixture to form a suspension;
   iv) forming the suspension into a clear solution;
   v) removing the solvent from the clear solution to form a clear viscous liquid; and
   vi) subjecting said clear viscous liquid to a procedure comprising dissolving said viscous liquid in the first solvent and drying the resultant solution at least once to form a first solid product from which said microparticles are thereafter formed.

27. The microparticles according to claim 26 wherein the solvent is removed in step v) by evaporation.

28. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of said polyester carboxylic acid end groups relative to said basic peptide groups, obtainable by a process comprising i) dissolving the carboxy-terminated polyester in a first solvent to form a first solution;

ii) adding the basic peptide to said first solution to form a suspension;

iii) adding a hydroxylic solvent to the suspension and forming the suspension into a clear solution; and iv) removing the solvent from the clear solution to form a first solid product which is in the form of microparticles, or from which said microparticles are thereafter formed.

29. The microparticles according to claim 28 wherein the first solid product is subjected to a procedure comprising dissolving said first solid product in the first solvent and drying the resultant solution at least once prior to the formation of said microparticles.

30. The microparticles according to claim 28 wherein in step iv) said first solid product is formed by a procedure selected from the group consisting of spray-drying, evaporation, freeze drying, phase separation coacervation, and spray-congealing.

31. Microparticles comprising a composition consisting essentially of a salt formed from a cation derived from a peptide containing one or more basic groups and an anion derived from a carboxy-terminated polyester, which composition has been prepared from at least an approximately stoichiometric equivalent of polyester carboxylic acid end groups relative to basic peptide groups, obtainable by a process comprising i) dissolving the carboxy-terminated polyester in a first solvent to form a first solution;

ii) dissolving the basic peptide in a hydroxylic solvent to form a second solution;

iii) adding said second solution to said first solution to form a third solution;

iv) removing the hydroxylic solvent and first solvent from said third solution to form a solid product;

v) dissolving the solid product in a third solvent which is a solvent for the polyester and a non-solvent for the peptide to form a fourth solution;

vi) dispersing said fourth solution in an aqueous phase to form an aqueous dispersion; and vii) drying said aqueous dispersion to form microparticles.

32. The microparticles according to claim 31 wherein the hydroxylic solvent and first solvent is removed in step iv) by evaporation.

33. The microparticles according to any of claims 24, 26, 28 and 31 wherein the first solvent is selected from the group consisting of dichloromethane and acetone.

34. The microparticles according to any one of claims 24, 26, 28 and 31 wherein the hydroxylic solvent is selected from the group consisting of methanol, ethanol and propylene-1,2-diol.

35. The microparticles according to any of claims 16, 17, 19, 22, 24, 26, 28 and 31 which composition has been prepared from a stoichiometric excess of polyester carboxylic acid end groups relative to basic peptide groups.

36. The microparticles according to any one of claims 16, 17, 19 or 22 obtainable by a process in which step ii) is carried out by a process selected from the group consisting of adding the first solution dropwise to liquid nitrogen; and adding the first solution into a mixture of solid carbon dioxide and hexane.

37. The microparticles according to claim 16 wherein the second solution is sterile-filtered prior to the second solvent being removed.

38. The microparticles according to any one of claims 16, 17, 19, or 22, wherein the first solvent is acetic acid.

39. The microparticles according to any one of claims 16, 17, 19, or 22, wherein the first solvent is dimethyl sulfoxide.

40. The microparticles according to any one of claims 16, 17, 19, or 22, wherein the second solvent is selected from dichloromethane and acetone.

41. The microparticles according to any one of claims 16, 17, 19, or 22, wherein the second solvent is selected from the group consisting of benzyl benzoate, benzyl alcohol, ethyl lactate, glyceryl triacetate, esters of citric acid, low molecular weight polyethylene glycols, alkoxypolyethylene glycols and polyethylene glycol acetates.

42. The microparticles according to any one of claims 24, 26, 28 or 31 wherein the first solvent is selected from the group consisting of benzyl benzoate, benzyl alcohol, ethyl lactate, glyceryl triacetate, esters of citric acid, low molecular weight polyethylene glycols, alkoxypolyethylene glycols and polyethylene glycol acetates.

43. The microparticles as claimed in claim 8 or 9 wherein the polyester is selected from the group consisting of polyesters derived from hydroxy-acids, polyesters derived from the polycondensation of diols with dicarboxylic acids, the polyesters derived from the polycondensation of polyols with polycarboxylic acids, and polyesters derived from ring opening polycondensation of acid dimers.

44. A microparticles as claimed in claim 8 or 9 wherein the peptide is pharmacologically active, and is selected from the group consisting of oxytocin, vasopressin, adrenocorticotrophic hormone (ACTH), epidermal growth factor (EGF), prolactin, luteinising hormone, follicle stimulating hormone, luliberin or luteinizing hormone releasing hormone (LHRH), insulin, somatostatin, glucagon, interferon, gastrin, tetragastrin, pentagastrin, urogastrone, secretin, calcitonin, enkephalins, endorphins, kyotorphin, taftsin, thymopoietin, thymosin, thymostimulin, thymic humoral factor, serum thymic factor, tumour necrosis factor, colony stimulating factors, motilin, bombesin, dinorphin, neurotension, cerulein, bradykinin, urokinase, kallikrein, substance P analogues and antagonists, angiotensin II, nerve growth factor, blood coagulation factor VII and IX, renin, bradykinin, tyrocidin, gramicidines, growth hormones, melanocyte stimulating hormone, thyroid hormone releasing hormone, thyroid stimulating hormone, parathyroid hormone, pancreozymin, cholecystokinin, human placental lactogen, human chorionic gonadotrophin, protein synthesis stimulating peptide, gastric inhibitory peptide, vasoactive intestinal peptide, platelet derived growth factor, growth hormone releasing factor, and bone morphogenic protein, and synthetic analogues and modifications and pharmacologically-active fragments thereof.

45. The microparticles as claimed in claim 8 or 9 wherein the basic peptide drug is a synthetic analogue of luteinising hormone releasing hormone, selected from the group consisting of buserelin ([D-Ser(Bu$^t$)$^6$, des-Gly-NH$_2$$^{10}$]-LHRH (1–9)NHEt), deslorelin ([D-Trp$^6$, des-Gly-NH$_2$$^{10}$]-LHRH (1–9)NHEt), fertirelin ([des-Gly-NH$_2$$^{10}$]-LHRH(1–9) NHEt), goserelin ([D-Ser(Bu$^t$)$^6$, Azgly$^{10}$]-LHRH), histrelin ([D-His(Bzl)$^6$, des-Gly-NH$_2$$^{10}$]-LHRH(1–9)NHEt), leuprorelin ([D-Leu$^6$, des-Gly-NH$_2$$^{10}$]-LHRH(1–9)NHEt), lutrelin ([D-Trp$^6$, MeLeu$^7$, des-Gly-NH$_2$$^{10}$]-LHRH(1–9)NHEt), nafarelin ([D-Nal)$^6$]-LHRH, and tryptorelin ([D-Trp$^6$]-LHRH), and pharmacologically active salts thereof.

46. The microparticles according to claim 31, wherein the aqueous phase comprises a viscosity-enhancing polymer.

47. The microparticles according to claim 31, wherein step vi) is carried out in the absence of carbon dioxide in an inert atmosphere.

\* \* \* \* \*

UNITED STATES PATENT AND TRADEMARK OFFICE
CERTIFICATE OF CORRECTION

PATENT NO.     : 5,889,110
DATED          : March 30, 1999
INVENTOR(S)    : Hutchinson Page 1 of 2

It is certified that error appears in the above-identified patent and that said Letters Patent is hereby corrected as shown below:

Col. 46, line 4, (Claim 7, line 2), change "carboxylic acid" to --carboxy--.

Col. 46, line 27 (Claim 11, line 4), after "vehicle", insert --.--, and delete the remainder of the claim.

Col. 46, line 36, (Claim 14, line 2), change "homo-" to --homo-polymer of the lactic acid--.

Col. 46, line 47 (Claim 16, line 6), change "carboxylic acid" to --carboxy--.

Col. 47, line 6, (Claim 17, line 6), change "carboxylic acid" to --carboxy--.

Col. 47, line 36 (Claim 19, line 6), change "carboxylic acid" to --carboxy--.

Col. 47, line 67 (Claim 22, line 6), change "carboxylic acid" to --carboxy--.

Col. 48, line 2 (apparent line 31) (Claim 24, line 6), change "carboxylic acid" to --carboxy--.

Col. 48, line 51 (apparent line 53) (Claim 26, line 6), change "carboxylic acid" to --carboxy--.

Col. 49, line 11 (Claim 28, line 6), change "carboxylic acid" to --carboxy--.

UNITED STATES PATENT AND TRADEMARK OFFICE
CERTIFICATE OF CORRECTION

PATENT NO. : 5,889,110
DATED : March 30, 1999
INVENTOR(S) : Hutchinson

It is certified that error appears in the above-identified patent and that said Letters Patent is hereby corrected as shown below:

Col. 49, line 39 (Claim 31, line 6), change "carboxylic acid" to --carboxy--.

Col. 50, lines 3-4 (Claim 35, line 3-4), change "carboxylic acid" to --carboxy--.

Signed and Sealed this

Seventh Day of March, 2000

Attest:

Q. TODD DICKINSON

Attesting Officer

Commissioner of Patents and Trademarks